(12) United States Patent
Schmaier et al.

(10) Patent No.: US 6,982,249 B1
(45) Date of Patent: Jan. 3, 2006

(54) BRADYKININ ANALOGS AS SELECTIVE INHIBITORS OF CELL ACTIVATION

(75) Inventors: Alvin H. Schmaier, Ann Arbor, MI (US); Ahmed A. K. Hasan, Dexter, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/402,732

(22) PCT Filed: Apr. 21, 1998

(86) PCT No.: PCT/US98/08015

§ 371 (c)(1),
(2), (4) Date: Dec. 1, 1999

(87) PCT Pub. No.: WO98/47522

PCT Pub. Date: Oct. 29, 1998

Related U.S. Application Data

(60) Provisional application No. 60/046,085, filed on Apr. 23, 1997.

(51) Int. Cl.
*C07K 5/09* (2006.01)
*C07K 7/00* (2006.01)

(52) U.S. Cl. .............................. 514/12; 514/13; 514/14; 514/15; 514/16; 514/17; 514/18; 530/324; 530/325; 530/326; 530/327; 530/328; 530/329

(58) Field of Classification Search ................... 514/15, 514/16, 17, 18, 12, 13, 14, 2, 21; 530/324, 530/325, 326, 327, 328, 329, 300

See application file for complete search history.

(56) References Cited

U.S. PATENT DOCUMENTS

| | | | |
|---|---|---|---|
| 4,585,757 A | 4/1986 | Pang et al. ..................... 514/18 |
| 4,638,047 A | 1/1987 | Szelke et al. ................ 530/332 |
| 4,693,993 A | 9/1987 | Stewart et al. ................. 514/14 |
| 4,870,017 A | 9/1989 | Ben-Bassat et al. |
| 4,923,963 A | 5/1990 | Stewart et al. ............... 530/314 |
| 5,231,080 A | 7/1993 | Scholkens ....................... 514/2 |
| 5,300,490 A | 4/1994 | Kunihiro et al. ................ 514/8 |
| 5,350,578 A | 9/1994 | Griffin et al. ............ 424/94.64 |
| 5,385,889 A | 1/1995 | Kyle et al. ..................... 514/15 |
| 5,409,899 A | 4/1995 | Fauchere et al. ............. 514/15 |
| 5,416,191 A | 5/1995 | Cheronis et al. ............ 530/314 |
| 5,446,131 A | 8/1995 | Maraganore ................ 530/326 |
| 5,472,945 A | 12/1995 | Schmaier et al. ............. 514/12 |
| 5,489,575 A | 2/1996 | Lee et al. ....................... 514/12 |
| 5,607,676 A | 3/1997 | Gevas et al. ........... 424/197.11 |

FOREIGN PATENT DOCUMENTS

| | | |
|---|---|---|
| AU | B-39431/89 | 5/1990 |
| WO | WO 92/17201 | 10/1991 |
| WO | WO 94/11021 | 5/1994 |
| WO | WO/96/41640 | 12/1996 |

OTHER PUBLICATIONS

Websters II, New Riverside University Dictionary 1259 (Anne H. Soukhanov ed., The Riverside Publishing Co. 1984).*

Stewart et al., "Bradykinin Chemistry: Agonists and Antagonists". In: Advance in Experimental Medicine and Biology, *New York: Plenum Press*, p. 585–589 (1983).

Martin et al., "Bradykinin Stimulates Phosphodiesteratic Cleavage of Phosphatidylcholine in Cultured Endothelial Cells", *Biochemical and Biophysical Research Communication*, 157(3): 1271–1279 (1988).

Chem abstr., vol. 107, No. 17, Oct. 26, 1987 (Columbus, Ohio), p. 146, column 2, the abstract No. 148141v, Alheid et al., "Endothelium–derived relaxing factor from cultured human endothelial cells inhibits aggregation of human platelets." *Thromb Res.*, 47(5): 561–71 (1987).

Chem. abstr., vol. 84, No. 21, May 24, 1976 (Colombus. Ohio), p. 417, column 2, the abstract No. 148985e, Shikawa et al., "Prostaglandin synthetase activity and hormone responsiveness in normal and SV40 transformed WI–38 fibroblasts", *J. of Cyclin Nucleotide Res.*, 2(2): 115–28 (1976).

Database CAplus on STN, Chemical Abstracts Service, (Columbus, OH), CAplus No. 1996:519830, Hasan et al., "Brandykinin and its metabolite, Arg–Pro–Pro–Gly–Phe, are selective inhibitors of alpha–thrombin–induced platelet activation", abstract Circulation 1996.

Chem. abstr., vol. 111, No. 9, Aug. 28, 1989 (Columbus, Ohio), p. 178, column 2, the abstract No. 71858g, Loeb et al., "Endotherlium–dependent potentiation of human platelet aggregation", *Thromb. Res.*, 54(5): 477–86 (1989).

Chem. abstr., vol. 93, No. 25, Dec. 22, 1980 (Columbus Ohio), p. 100, column 1, the abstract No. 231243t, Imai et al., "Effects of prostacyclin on platelet aggregation as studied with 'filter–loop' technique in the flowing blood of the dog", *Artery*, 8(1): 90–5 (1980).

Ngo et al., "Computational Complexity Protein Structure Problem and the Levinthal Paradox", *The Protein Folding Prediction and Tertiary Structure Prediction*, pp. 491–495 (1994).

(Continued)

*Primary Examiner*—Bruce R. Campell
*Assistant Examiner*—Anish Gupta
(74) *Attorney, Agent, or Firm*—Drinker Biddle & Reath LLP

(57) ABSTRACT

The present invention provides bradykinin peptide analogs, compositions, and methods of inhibiting thrombin-induced platelet and other cell activation. The bradykinin analogs comprise single or multiple peptide segments. The invention also provides a method for identifying compounds that selectively inhibit thrombin-induced platelet and other cell activation.

12 Claims, 8 Drawing Sheets

OTHER PUBLICATIONS

Hasan, et al., "The Carboxyl Terminus of Bradykinin and Amino Terminus of the Light Chain of Kininogens Comprise and Endothelial Cell Binding Domain", *The Journal of Biological Chemistry*, 269(50): 31822–31830 (Dec. 16, 1994).

Wirth, et al., "Hoe 140 a new potent and long acting bradykinin–antagonist: in vivo studies", *British Journal of Pharmacology*, 102(3): 774–777 (Mar., 1991).

Vu, et al., "Molecular Cloning of a Functional Thrombin Receptor Reveals a Novel Protelytic Mechanism of Receptor Activation", *Cell*, 64: 1057–1068 (Mar. 22, 1991).

Puri, et al., "Inhibition of Thrombin–Induced Platelet Aggregation By High Molecular Weight Kininogen", *Transactions of the Association of American Physicans*, C: 232–240 (1987).

Puri, et al., "Cleavage of A 100 kDa Membrane Protein (Aggregin) During Thrombin–Induced Platelet Aggregation Is Mediated By The High Affinity Thrombin Receptors", *Biochemical and Biophysical Research Communications*, 162(3): 1017–1024 (Aug. 15, 1989).

Puri, et al., "Reocclusion after thrombolytic therapy: strategies for inhibiting thrombin–induced platelet aggregation", *Blood Coagulation and Fibrinolysis*, 4: 465–478 (1993).

Puri, et al., "High Molecular Weight Kininogen Inhibits Thrombin–Induced Platelet Aggregation and Cleavage of Aggregin by Inhibiting Binding of Thrombin to Platelets", *Blood*, 77(3): 500–507 (Feb. 1, 1991).

Meloni, et al., "Low Molecular Weight Kininogen Binds to Platelets to Modulate Thrombin–Induced Platelet Activation", *The Journal of Biological Chemistry*, 265(11): 6786–6794 (Apr. 13, 1991).

Hasan et al., "Bradykinin And Related Peptides Selectively Inhibit α–Thrombin's Ability To Activate The Platelet Thrombin Receptor", *Thrombosis and Haemostasis*, 73(6): 94 (Abstract) (Jun., 1995).

Imai, et al. "Effects of Prostacyclin on Plateet Aggregation as Studied With "Filter Loop" Technique in the Flowying of Blood of the Dog", *Artery* 8(1): 63–72 (1980).

J.A. Parsons, "Peptide Hormones", published 1976 by University park Press (Baltimore), p. 1–7.

Park et al., "Synthesis of Peptides by the Solid Phase Method, III. Bradykinin: Fragments and Analogs", *Can. J. Biochem.*, 56: 92–100 (1978).

Hasan et al., "Bradykinin and Its Metabolite, Arg–Pro–Pro–Gly–Phe, Are Selective Inhibitors of α–Thrombin–Induced Platelet Activation", *Circulation*, 94(3): 517–528 (Aug 1, 1996).

* cited by examiner

SEQUENCE LISTING

```
<160> NUMBER OF SEQ ID NOS: 12

<210> SEQ ID NO 1
<211> LENGTH: 64
<212> TYPE: PRT
<213> ORGANISM: Artificial Sequence
<220> FEATURE:
<223> OTHER INFORMATION: bradykinin analog

<400> SEQUENCE: 1

Cys Asn Ala Glu Val Tyr Val Val Pro Trp Glu Lys Lys Ile Tyr Pro
 1               5                  10                  15

Thr Val Asn Cys Gln Pro Leu Gly Met Ile Ser Leu Met Lys Arg Pro
            20                  25                  30

Pro Gly Phe Ser Pro Phe Arg Ser Ser Arg Ile Gly Glu Ile Lys Glu
        35                  40                  45

Glu Thr Thr Val Ser Pro Pro His Thr Ser Met Ala Pro Ala Gln Asp
    50                  55                  60

<210> SEQ ID NO 2
<211> LENGTH: 12
<212> TYPE: PRT
<213> ORGANISM: Artificial Sequence
<220> FEATURE:
<223> OTHER INFORMATION: bradykinin analog

<400> SEQUENCE: 2

Asn Ala Thr Leu Asp Pro Arg Ser Phe Leu Leu Arg
 1               5                  10

<210> SEQ ID NO 3
<211> LENGTH: 9
<212> TYPE: PRT
<213> ORGANISM: Artificial Sequence
<220> FEATURE:
<223> OTHER INFORMATION: bradykinin analog

<400> SEQUENCE: 3

Asn Pro Asn Asp Lys Tyr Glu Pro Phe
 1               5

<210> SEQ ID NO 4
<211> LENGTH: 6
<212> TYPE: PRT
<213> ORGANISM: Artificial Sequence
<220> FEATURE:
<223> OTHER INFORMATION: bradykinin analog

<400> SEQUENCE: 4

Ser Phe Leu Leu Arg Asn
 1               5
```

-continued

```
<210> SEQ ID NO 5
<211> LENGTH: 9
<212> TYPE: PRT
<213> ORGANISM: Artificial Sequence
<220> FEATURE:
<223> OTHER INFORMATION: bradykinin analog

<400> SEQUENCE: 5

Arg Pro Pro Gly Phe Ser Pro Phe Arg
  1               5

<210> SEQ ID NO 6
<211> LENGTH: 5
<212> TYPE: PRT
<213> ORGANISM: Artificial Sequence
<220> FEATURE:
<223> OTHER INFORMATION: bradykinin analog

<400> SEQUENCE: 6

Arg Pro Pro Ala Phe
  1               5

<210> SEQ ID NO 7
<211> LENGTH: 5
<212> TYPE: PRT
<213> ORGANISM: Artificial Sequence
<220> FEATURE:
<223> OTHER INFORMATION: bradykinin analog

<400> SEQUENCE: 7

Arg Pro Pro Gly Phe
  1               5

<210> SEQ ID NO 8
<211> LENGTH: 7
<212> TYPE: PRT
<213> ORGANISM: Artificial Sequence
<220> FEATURE:
<223> OTHER INFORMATION: bradykinin analog

<400> SEQUENCE: 8

Leu Asn Ala Glu Asn Asn Ala
  1               5

<210> SEQ ID NO 9
<211> LENGTH: 5
<212> TYPE: PRT
<213> ORGANISM: Artificial Sequence
<220> FEATURE:
<223> OTHER INFORMATION: bradykinin analog

<400> SEQUENCE: 9

Arg Pro Pro Gly Cys
  1               5

<210> SEQ ID NO 10
<211> LENGTH: 5
<212> TYPE: PRT
<213> ORGANISM: Artificial Sequence
<220> FEATURE:
<223> OTHER INFORMATION: bradykinin analog

<400> SEQUENCE: 10

Phe Ser Pro Phe Arg
  1               5
```

```
<210> SEQ ID NO 11
<211> LENGTH: 4
<212> TYPE: PRT
<213> ORGANISM: Artificial Sequence
<220> FEATURE:
<223> OTHER INFORMATION: bradykinin analog - part of heterodimer

<400> SEQUENCE: 11

Arg Pro Pro Lys
 1

<210> SEQ ID NO 12
<211> LENGTH: 4
<212> TYPE: PRT
<213> ORGANISM: Artificial Sequence
<220> FEATURE:
<223> OTHER INFORMATION: bradykinin analog - part of heterodimer

<400> SEQUENCE: 12

Arg Pro Pro Asp
 1
```

BRADYKININ ANALOGS AS SELECTIVE INHIBITORS OF CELL ACTIVATION

CROSS-REFERENCE TO RELATED APPLICATIONS

This application claims the benefit of U.S. provisional application Ser, No. 60/046,085, filed Apr. 23, 1997.

REFERENCE TO GOVERNMENT GRANT

The invention described herein was made, in part, in the course of work supported by the National Heart Lung and Blood Institute under Grant Nos. HL35553, HL55907, HL52779, and HL56415. The government has certain rights in the invention.

FIELD OF THE INVENTION

This invention relates to the inhibition of thrombin-induced cell activation, and to the identification of compounds that inhibit thrombin-induced cell activation.

BACKGROUND OF THE INVENTION

Bradykinin is a vasoactive peptide released from the precursor plasma kininogens by kallikrein and other enzymes (Silva et al., *Amer. J. Physiol.* 156: 261–274 (1949)). Bradykinin has been described to have multiple physiologic functions, including the stimulation of prostacyclin production (Hong, S. L., *Thromb. Res.* 18, 787 (1980); Crutchley et al., *Biochim Biophy Acta* 751, 99 (1983)) and the stimulation of the release of plasminogen activators (Smith et al., *Blood* 66, 835 (1983)). Bradykinin induces superoxide formation and endothelium-dependent smooth muscle hyperpolarization (Holland, J. A. et al., *J. Cell Physiol.* 143, 21 (1990); Nakashima, M. et al., *J. Clin. Invest.* 92, 2867 (1993)). Along with acetylcholine, bradykinin is the major inducer of nitric oxide formation (Palmer, R. M. J. et al., *Nature* 327, 524 (1987)). Bradykinin has been characterized to produce vasodilation in most vascular beds which in the coronary artery circulation results in increased blood flow (Line et al., *J. Mol. Cell Cardiol.* 24, 909 (1992)). These latter features have led some to characterize bradykinin as a cardioprotective agent (Line et al., supra; Gohlke et al., *Hypertension* 23, 411 (1994); Parratt et al., *Cardiovascular Research* 28, 183 (1994); Zanzinger et al., *Cardiovascular Research* 28, 209 (1994)). Bradykinin's elevation by angiotensin converting enzyme inhibitors is believed to be the mechanism by which these drugs promote their beneficial effects on heart failure.

In addition to the delivery of bradykinin, its parent proteins, high (HK) and low (LK) molecular weight kininogens, also have the ability to be selective inhibitors of α-thrombin, inhibiting α-thrombin's ability to activate cells without interfering with its enzymatic ability (Meloni et al., *J. Biol. Chem.* 266, 6786 (1991); Puri et al., *Blood* 77, 500 (1991)). This activity was believed to be a unique function for the kininogens; one which had not been ascribed to other proteins. Most naturally occurring human protein inhibitors of α-thrombin are directed towards its protease activity. HK and LK are selective inhibitors of thrombin's ability to activate platelets by blocking α-thrombin from binding to the platelet membrane (Meloni et al., supra; Puri et al., supra). This activity of the kininogens appeared to be localized to domain 3 on their heavy chain since isolated domain 3 retains that activity (Jiang et al., *J. Biol. Chem.* 267, 3712 (1992)).

Inhibition of platelet activation by domain 3 is observed by a marked decrease in the platelet's ability to aggregate and secrete their granule contents. The granule contents comprise proteins which participate in hemostasis, thrombosis, and the inflammatory response. Inhibition of endothelial cell activation may similarly be observed by a decrease in secretion of endothelial cell contents such as tissue plasminogen activator and von Willebrand factor.

The isolated domain 3 from a tryptic digest of LK, like its parent proteins HK and LK, functions to inhibit cell activation by blocking thrombin binding to its target cells. This polypeptide is a selective inhibitor of thrombin-induced platelet activation. Administration of domain 3 in vitro therefore does not impact on induction of platelet activation by physiological substances other than thrombin, such as, for example collagen, adenosine diphosphate, epinephrine and platelet activating factor.

Interventional procedures for coronary artery disease such as coronary thrombolysis or percutaneous transluminal coronary angioplasty have reduced mortality from acute coronary thrombosis. However, after intracoronary thrombolysis with lytic agents, the reocclusion rate is high. The major cause for reocclusion is platelet thrombus. When artificial dacron grafts are anastomosed to human arteries, up to 30% of all patients will develop a platelet thrombosis within hours of surgery. This expected high complication rate frequently requires an additional operation with attendant complications. Thus, additional therapies are needed to prevent these reocclusion events due to platelet thrombi.

Two competing classes of antiplatelet agents for the prevention of coronary thrombosis are being considered. One class of agents, including monoclonal antibody 7E3, aims to block the final common pathway of platelet activation by inhibiting glycoprotein IIb/IIIa (GPIIb/IIIa), integrin $\alpha_{IIb}\beta_3$. 7E3 is an effective agent, but it is a murine antibody and is antigenic in humans. A second class of antiplatelet agents inhibit a presumed, primary initiating agent of platelet activation, α-thrombin. Infusions of Phe-Pro-Arg-chloromethylketone (PPACK), a potent inhibitor of α-thrombin's proteolytic activity, prolongs the bleeding time, a crude measure of platelet function (Hanson, S. R. et al., *Proc. Natl. Acad. Sci.* 85, 3184–3188 (1988)). The first generation of potent α-thrombin proteolytic inhibitors to enter into clinical trials is a recombinant product derived from medicinal leeches, hirudin. This compound, which is a small molecular mass and is not considered to be antigenic, is a potent anti-thrombin. A synthetic analog of hirudin, hirulog, combines the anion exosite I binding properties of hirudin with the proteolytic inhibitory activity of PPACK. In Phase III clinical trials, both drugs were effective inhibitors of platelet activation. The tradeoff for effective anticoagulation, however, was increased hemorrhage into brain leading to the termination of three clinical trials. These non-selective inhibitors of α-thrombin have an antithrombotic efficiency dose close to their toxicity dose and are not clinically tolerated and, thus, may never have commercial significance.

An ideal anti-thrombotic to prevent arterial thrombosis would be one which prevents platelet and endothelial cell activation without preventing the proteolytic activity of α-thrombin to clot fibrinogen and activate protein C, factor XIII, and factors V and VIII. Only two known proteins, high molecular weight (HK) and low molecular weight (LK) kininogens, are naturally occurring selective anti-thrombins (Meloni, F. J. et al., *J. Biol. Chem.* 266; 6786–6794 (1991); Puri, R. N. et al., *Blood* 77:500–507 (1991)). Both low and high molecular weight kininogens have identical amino acid sequences from their amino-terminus through 12 amino acids beyond the carboxy-terminus of bradykinin. LK and HK share a common heavy chain (62 kDa), the bradykinin (BK) moiety (0.9 kDa), and the first 12 amino acids of the amino terminal portion of each of their "light chains" (Takagaki, Y. et al., *J. Biol. Chem.* 260:8601–8609 (1985); Kitamura, N. et al., *J. Biol. Chem.*, 260:8610–8617 (1985)). This identity corresponds to residues 1 through about residue 383. See Salveson et al., *Biochem J.* 234, 429 (1986); Kellerman et al., *Eur. J. Biochem.* 154, 471 (1986). They diverge in the size of their light chains; the light chain of LK is 4 kDa; that of HK is 56 kDa. Takagaki et al., supra; Kitamura et al., supra.

There is a need for improved methods of identification, as well as the identification of new compounds which specifically inhibit thrombin-induced platelet or other cell activation, and for compounds which prevent platelet aggregation.

SUMMARY OF THE INVENTION

The invention comprises a method of inhibiting thrombin-induced platelet or other cell activation comprising administering to an individual in need of such treatment an effective amount of a compound which inhibits thrombin activation of platelets or other cells which express the thrombin receptor, wherein said compound has the formula:

$$X_1\text{-Arg-Pro-Pro-}X_2 \quad (1)$$

wherein:

$X_1$ is from zero to thirty natural or synthetic amino acids; and $X_2$ is from zero to thirty natural or synthetic amino acids, sprovided that the N-terminal amino acid of $X_2$ is not glycine.

One embodiment of the invention comprises administering a compound according to formula 1, wherein $X_1$ is zero to seven amino acids and $X_2$ is zero to nine amino acids.

A preferred embodiment of the invention comprises administering a compound according to formula 1, wherein $X_1$ is from zero to thirty amino acids from amino acids 1–30 of SEQ ID NO: 1.

A most preferred embodiment of the invention comprises administering a compound according to formula I wherein the compound has the formula Arg-Pro-Pro. Another most preferred embodiment of the invention comprises administering a compound according to formula I wherein the compound has the sequence Arg-Pro-Pro-Ala-Phe (SEQ ID NO:6).

The invention also comprises a method of inhibiting thrombin-induced platelet or other cell activation comprising administering to an individual in need of such treatment an effective amount of a compound which inhibits thrombin activation of platelets or other cells, wherein said compound comprises two or more segments having the amino acid sequence $X_1$-Arg-Pro-Pro-$X_2$, and the compound has the formula:

$$\text{L-}(X_1\text{-Arg-Pro-Pro-}X_2)_n \quad (II)$$

wherein:

L is a linker comprising a covalent bond or chemical group;

$X_1$, which may be the same or different in each segment, is from zero to thirty natural or synthetic amino acids;

$X_2$, which may be the same or different in each segment, is from zero to thirty natural or synthetic amino acids;

the N-terminal amino acid of $X_2$ is not glycine; and n is an integer from two to twenty.

One embodiment of the invention comprises administering a compound according to formula II, wherein $X_1$ is zero to seven amino acids and $X_2$ is zero to nine amino acids.

Another embodiment of the invention comprises administering a compound according to formula II wherein the compound has the formula:

$$\text{L-(Arg-Pro-Pro-}X_2)_n$$

A preferred embodiment comprises administering a compound according to formula II wherein the compound has the formula:

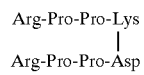

Arg-Pro-Pro-Lys
|
Arg-Pro-Pro-Asp

Another preferred embodiment comprises administering a compound according to formula II wherein the compound has the formula:

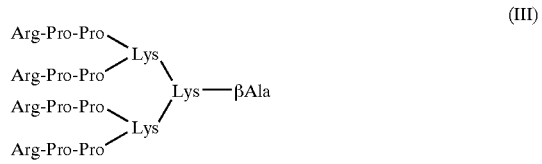

(III)

The invention further comprises a method for preventing platelet aggregation comprising administering to an individual in need of such treatment an effective amount of a compound according to formula I, II, or III.

The invention further comprises a method for inhibiting ADP-induced platelet activation in vivo comprising administering to an individual in need of such treatment an effective amount of a compound according to formula I, II, or III.

The invention also comprises a compound according to formula I, II, or III. In a preferred embodiment the compound has the formula:

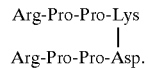

Arg-Pro-Pro-Lys
|
Arg-Pro-Pro-Asp.

Another preferred embodiment is a compound according to formula III.

The invention further comprises a pharmaceutical composition comprising a pharmaceutically acceptable carrier and a compound according to formula I, II, or III.

The invention also comprises the use of a compound according to formula I, II, or III for the preparation of a medicament for inhibiting thrombin-induced platelet or other cell activation, or for preventing platelet aggregation.

The invention further provides a method for identifying compounds that selectively inhibit thrombin-induced platelet and other cell activation comprising measuring the ability of the compounds to bind to the thrombin cleavage site on the thrombin receptor. In a preferred embodiment the compounds are present in a combinatorial library. In a more preferred embodiment the method further comprises (a) measuring the ability of the compounds to inhibit thrombin-induced platelet aggregation; and (b) measuring the ability of the compounds to inhibit thrombin-induced calcium mobilization in fibroblasts.

DETAILED DESCRIPTION OF THE INVENTION

Definitions

Figure 1:
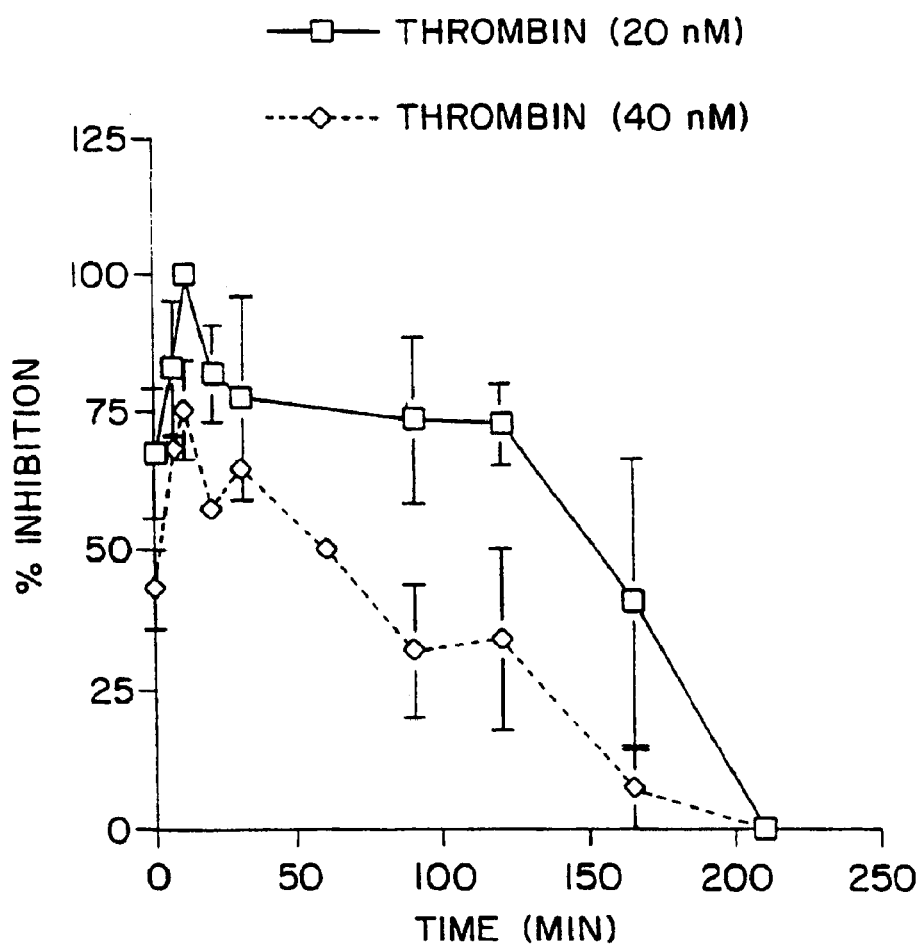
FIG. 1 shows the prolonged inhibition of γ-thrombin-induced platelet aggregation of rabbit platelets ex vivo after the in vivo infusion of RPPGF (SEQ ID NO:7).

"Natural amino acid" means any of the twenty primary, naturally occurring amino acids which typically form peptides, polypeptides, and proteins.

"Synthetic amino acid" means any other amino acid, regardless of whether it is prepared synthetically or derived from a natural source. As used herein, "synthetic amino acid" also encompasses chemically modified amino acids, including but not limited to salts, derivatives (such as amides), and substitutions.

"Human kininogen" means, unless otherwise indicated, both high and low molecular weight forms of any kininogen molecule, in all its various forms derived from human plasma, platelets, endothelial cells, granulocytes, or skin or other tissues or organs, regardless of whether it is found in the fluid or the tissue phase.

"Light chain", when referring or relating to human kininogen, means the 56 kDa intermediate plasma kallikrein-cleavage fragment of HK which has the ability to correct the coagulant defect in total kininogen-deficient plasma.

"Heavy chain", when referring or relating to human kininogen, means the 64 kDa kallikrein-cleavage fragment of HK or LK, which is free of bradykinin and "light chain".

"Domain 3", with respect to the kininogen heavy chain, means the trypsin-cleavage fragment of the human kininogen heavy chain which is about 21 kDa.

"Bradykinin" (BK) means the nonapeptide having the sequence SEQ ID NO: 5.

"BK analog" means a compound comprising an amino acid sequence analogous to all or part of the sequence of the nonapeptide bradykinin, which is capable of inhibiting α-thrombin from cleaving its receptor on platelets and other cells, such that the peptide prevents the alteration or loss of the SPAN12 epitope on the thrombin receptor, and blocks cleavage of a peptide, NAT12 (SEQ ID NO:2), which spans the α-thrombin cleavage site on the thrombin receptor.

"Heterodimer" means a compound comprising two different single-chain BK analogs joined by a linker.

"Homodimer" means a compound comprising two identical single-chain BK analogs joined by a linker. "Symmetric homodimer" means a homodimer in which the linker joins amino acids which occupy the same position in the single chain BK analogs. "Asymmetric homodimer" means a homodimer in which the linker joins amino acids which occupy different positions in the single chain BK analogs.

Abbreviations

Some of the nomenclature of the subject matter of the present invention involves lengthy terms. It is customary for those skilled in the art to abbreviate these terms in a manner well-known to the art. These general and customary abbreviations are set forth below and may be utilized in the text of this specification.

ATAP138: monoclonal antibody specific for an epitope on the thrombin receptor, which epitope is preserved following α-thrombin cleavage of the receptor BK: bradykinin D3: domain 3 of kininogen EDTA: ethylenediaminetetraacetic acid FITC: fluorescein isothiocyanate HBTU: 2-(1-H-benzotriazole-1-YL)-1,1,3,3-tetramethyl-uroniumhexofluorophosphate HOBt: 1-hydroxybenzotriazole HK: human high molecular weight kininogen LK: human low molecular weight kininogen NAT12: peptide sequence Asn-Ala-Thr-Leu-Asp-Pro-Arg-Ser-Phe-Leu-Leu-Arg (SEQ ID NO:2), which spans the α-thrombin cleavage site on the thrombin receptor PGE1: prostaglandin E1

SPAN12: monoclonal antibody specific for the sequence Asn-Ala-Thr-Leu-Asp-Pro-Arg-Ser-Phe-Leu-Leu-Arg (SEQ ID NO:2) which spans the α-thrombin cleavage site on the thrombin receptor TRAP: thrombin receptor activation peptide, which has the amino acid sequence Ser-Phe-Leu-Leu-Arg-Asn (SEQ ID NO:4)

The invention is directed to a method for preventing thrombosis by the use of BK analogs, bradykinin sequence-related analogous peptides that act as selective anti-thrombins. The BK analogs are selective anti-thrombins because they are able to inhibit human α-thrombin and γ-thrombin from activating platelets and other cells without interfering with α-thrombin's ability to proteolyze its various substrates, e.g., fibrinogen and factor XIII. Most known thrombin inhibitors, hirudin, hirulog and PPACK, interfere with α-thrombin's action by blocking all of its proteolytic activity. Use of these proteolytic inhibitors to inhibit α-thrombin activation of platelets may result in excessive anticoagulation and hemorrhage. The BK analogs utilized in the present method allow for inhibition of thrombin-induced cell activation (e.g. platelet activation, mitogenesis) without interfering with α-thrombin's enzymatic activity on other substrates, such as proteolysis of fibrinogen and activation of factor XIII. BK analogs may be used to prevent arterial occlusions which occur in coronary thrombosis and stroke.

The BK analogs of the present invention block 1 nM γ-thrombin from activating platelets in the presence of 100 mg/dl fibrinogen and in platelet-rich plasma.

The BK analogs of the present invention do not appear to inhibit platelet activation by the same mechanism as intact kininogen and its isolated domain 3, because the BK analogs do not inhibit $^{125}$-α-thrombin binding to platelets, as does a molar excess of purified HK, LK, or isolated domain 3.

Without wishing to be bound by any theory, the BK analogs of the present invention are believed to inhibit platelet and other cell activation by inhibiting α-thrombin from cleaving its receptor, which is expressed on platelets and other cells. The BK analogs thus have the ability to inhibit thrombin-induced platelet activation by blocking cleavage of the thrombin receptor and subsequent activation of platelets by exposure of the new amino terminus of the cleaved receptor.

Administration of a BK analog as described herein comprises a therapeutic method for inhibiting thrombin-induced activation of platelets, endothelial cells, brain cells, fibroblasts, smooth muscle cells, or other cells that express the thrombin receptor. This function inhibits platelet thrombus formation and other activities mediated by the thrombin receptor.

The thrombin receptor peptide NAT12 and monoclonal antibodies SPAN12 and ATAP138 are useful for characterizing the compounds, compositions, and methods of the present invention, as illustrated in Example 1. NAT12 has a sequence, Asn-Ala-Thr-Leu-Asp-Pro-Arg-Ser-Phe-Leu-Leu-Arg (SEQ ID NO:2), which spans the α-thrombin cleavage site on the thrombin receptor.

Monoclonal antibodies to the thrombin receptor, SPAN12 and ATAP138, were obtained from Dr. Lawrence F. Brass of the University of Pennsylvania, and were prepared according to the method of Brass et al., *J. Biol. Chem.* 267, 13795 (1992). Monoclonal antibody SPAN12 was reared to the 12 amino acids. Asn-Ala-Thr-Leu-Asp-Pro-Arg-Ser-Phe-Leu-Leu-Arg (SEQ ID NO:2), that bridge the α-thrombin cleavage site on the thrombin receptor. Monoclonal antibody ATAP138 recognizes an epitope, Asn-Pro-Asn-Asp-Lys-Tyr-Glu-Pro-Phe (SEQ ID NO:3), on the thrombin receptor which is preserved after cleavage by α-thrombin. When α-thrombin cleaves the thrombin receptor, it eliminates the epitope which is recognized by the SPAN12 antibody but not the epitope which is recognized by the ATAP138 antibody.

The complete sequence for human kininogen heavy chain is found in Kellerman et al., *Eur. J Biochem.* 154:471–478 (1986), the entire disclosure of which is incorporated herein by reference. The amino acid sequence of the human kininogen parent segment which spans kininogen amino acid residues 333 to 396, is given herein as SEQ ID NO:1. The core peptide sequence Arg-Pro-Pro corresponds to kininogen amino acid residues 363–65.

According to the present invention, naturally occurring or synthetic amino acids having the general formula

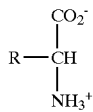

where R is a hydrogen atom or an organic side chain, are added to either the carboxyl or amino terminus of a peptide comprising the core sequence Arg-Pro-Pro, in order to form chain expansion analogs. Up to thirty amino acids may be added to either the carboxyl or amino terminus of the core sequence. Preferably, from zero to seven amino acids are added to the amino terminus, and zero to nine amino acids are added to the carboxyl terminus of the core sequence. An example of the BK analogs included in this invention is the BK analog SEQ ID NO:6, which has the sequence Arg-Pro-Pro Ala-Phe. Another example is the tripeptide Arg-Pro-Pro.

According to one embodiment of the invention, the BK analog has the sequence $X_1$-Arg-Pro-Pro-$X_2$, wherein $X_1$ is from zero to thirty amino acids from the amino terminal portion of the kininogen heavy chain parent segment (amino acids 1–30 of SEQ ID NO: 1) and $X_2$ is from zero to thirty natural or synthetic amino acids, provided that the N-terminal amino acid of $X_2$ is not glycine.

In another embodiment of the invention, the BK analog has the sequence $X_1$-Arg-Pro-Pro-$X_2$, wherein $X_1$ is from zero to seven amino acids from the amino terminal portion of the kininogen heavy chain parent segment (amino acids 24–30 of SEQ ID NO:1) and $X_2$ is from zero to nine natural or synthetic amino acids, provided that the N-terminal amino acid of $X_2$ is not glycine.

According to another embodiment of the invention, two or more single-chain BK analogs are joined by one or more linkers, L, to form homodimers, heterodimers, trimers, or other multimers. The linker can be either a covalent bond or a chemical group. The number of single-chain BK analogs that can be joined is from two to thirty-two. Preferably, the number of BK analogs joined is from two to twenty, more preferably from two to eight, and most preferably, from two to four. The BK analogs to be joined can be identical or they can be different. A heterodimer is comprised of two different single-chain BK analogs; a homodimer is comprised of two identical single-chain BK analogs. The multimers can be symmetric or asymmetric. A "symmetric homodimer" means a homodimer in which the linker joins amino acids which occupy the same position in the single chain BK analogs. An "asymmetric homodimer" means a homodimer in which the linker joins amino acids which occupy different positions in the single chain BK analogs.

An example of a covalent bond linking two single-chain BK analogs is the disulfide bond formed by the oxidation of two single chain BK analogs containing cysteine amino acids. This may require initially modifying the parent peptide so that the peptide includes a Cys residue in the appropriate position. Cysteine residues on single-chain BK analogs can be oxidized to form BK analog dimers by dissolving 1 mg of the single-chain peptide in 1.5 ml of 0.1% (v/v) 17.5 mM acetic acid, pH 8.4, followed by flushing with nitrogen and then 0.01 M $K_2Fe(CN)_6$. After incubation for one hour at room temperature, the dimer peptide is purified by HPLC.

Another example of a suitable covalent bond for linking two single-chain BK analogs is the amide bond formed by reacting the amino group of a lysine amino acid residue on one chain with the carboxylic acid group of a glutamic or aspartic amino acid residue of another chain.

Alternatively, the linking group can be formed by the covalent bond between two single-chain BK analogs using a cross-linking reagent. For example, homodimers and heterodimers can be prepared by first preparing S-(-N-hexylsuccinimido)-modified peptide monomers according to the method of Cheronis et al., *J Med. Chem.* 37: 348 (1994). N-hexylmaleimide, a precursor for the modified peptide monomers, is prepared from N-(methoxycarbonyl) maleimide and N-hexylamine by mixing the two compounds in saturated $NaHCO_3$ at 0° C. according to the procedure of Bodanszky and Bodanszky, *The Practice of Peptide Synthesis;* Springer-Verlag, New York, pp. 29–31 (1984). The product of the resulting reaction mixture is isolated by extraction into ethyl acetate, followed by washing with water, dried over $Na_2SO_4$, and is then concentrated in vacuo to produce N-hexylmaleimide as a light yellow oil. S-(N-Hexylsuccinimido)-modified peptide monomers are then prepared from a cysteine-containing peptide (monomer) and N-hexylmaleimide by mixing one part peptide with 1.5 parts N-hexylmaleimide in dimethylfonmamide (3.3 ml/mM peptide) followed by addition to 30 volumes of 0.1 M ammonium bicarbonate, pH 7.5. The S-alkylation reaction carried out in this manner is complete in 30 min. The resulting S-(N-hexylsuccinimido)-modified peptide monomer is purified by preparative reverse-phase HPLC, followed by lyophilization as a fluffy, white powder.

Bissuccinimidohexane peptide dimers, either as homodimers or heterodimers, may be prepared according to the method of Cheronis et al., supra from cysteine-substituted peptides in the same or different positions, respectively. A mixture of one part bismaleimidohexane is made with two parts peptide monomer in dimethylformamide (3.3 ml/mM peptide) followed by addition to 0.1 ammonium bicarbonate, pH 7.5. The reaction mixture is stirred at room temperature and is usually completed within 30 min. The resulting bissuccinimidohexane peptide dimer is purified by preparative reverse-phase HPLC. After lyophilization the material is a fluffy, white powder.

Covalently cross-linked BK analog dimers of the present invention may be prepared by utilizing homobifunctional cross-linking reagents, e.g., disuccinimidyl tartrate, disuccinimidyl suberate, ethylene glycolbis(succinimidyl succinate), 1,5-difluoro-2,4-dinitrobenzene ("DFNB"), 4,4'-diisothiocyano-2,2'-disulfonic acid stilbene ("DIDS"), and bismaleimidohexane ("BMH"). The cross-linking reaction occurs randomly between the single-chain BK analogs.

Alternatively, heterobifunctional cross-linking reagents may be employed. Such agents include, for example, N-succinimidyl-3-(2-pyridyldithio)propionate ("SPDP"), sulfosuccinimidyl-2-(p-azidosalicylamido)ethyl-1-3'-dithiopropionate ("SASD", Pierce Chemical Company, Rockford, Ill.), N-maleimidobenzoyl-N-hydroxysuccinimidyl ester ("MBS"), m-maleimidobenzoylsulfosuccinimide ester ("sulfo-MBS"), N-succinimidyl(4-iodoacetyl)aminobenzoate ("SIAB"), succinimidyl 4-(N-maleimidomethyl)-cyclohexane-1-carboxylate ("SMCC"), succinimidyl-4-(p-maleimidophenyl)butyrate ("SMPB"), sulfosuccinimidyl(4-iodoacetyl)aminobenzoate ("sulfo-SIAB"), sulfosuccinimidyl 4-(N-maleimidomethyl)cyclohexane-1-carboxylate ("sulfo-SMCC"), sulfosuccinimidyl 4-(p-maleimidophenyl)-butyrate("sulfo-SMPB"), bromoacetyl-p-arninobenzoyl-N-hydroxy-succinimidyl ester, iodoacetyl-N-hydroxysuccinimidyl ester, and the like.

For heterobifunctional cross-linking, a first single-chain BK analog is derivatized with, e.g., the N-hydroxysuccinimidyl portion of the bifunctional reagent, and the derivatized BK analog is purified by gel filtration. Next, a second single-chain BK analog (which may or may not be the same or different from the first BK analog) is reacted with the second functional group of the bifunctional reagent, assuring a directed sequence of binding between components of the BK dimer.

Typical heterobifunctional cross-linking agents for forming protein-protein conjugates have an amino-reactive N-hydroxysuccinimide ester (NHS-ester) as one functional group and a sulfhydryl reactive group as the other functional group. First, epsilon-amino groups of surface lysine residues of the first single chain BK analog are acylated with the NHS-ester group of the cross-linking agent. The second single chain BK analog, possessing free sulfhydryl groups, is reacted with the sulfhydryl reactive group of the cross-linking agent to form a covalently cross-linked dimer. Common thiol reactive groups include maleimides, pyridyl disulfides, and active halogens. For example, MBS contains a NHS-ester as the amino reactive group, and a maleimide moiety as the sulfhydryl reactive group.

Photoactive heterobifunctional cross-linking reagents, e.g., photoreactive phenyl azides, may also be employed. One such reagent, SASD, may be linked to a single-chain BK analog via its NHS-ester group. The conjugation reaction is carried out at pH 7 at room temperature for about 10 minutes. Molar ratios between about 1 and about 20 of the cross-linking agent to the BK analog may be used.

The purified, derivatized BK analog is collected by affinity chromatography using a matrix having affinity for BK analogs, e.g., a polyclonal antibody reared to the BK analog. Antibody for this purpose may be prepared by coupling the BK analog to key hole limpet hemocyanin using 1-ethyl-3-(3-dimethylaminopropyl)-carbodiimide-HCL (Goodfriend et al., *Science* 144, 1344 (1964)). The resulting conjugate is used to immunize rabbits by the procedure of Müller-Esterl et al., *Methods Enzymol* 163, 240 (1988) to produce anti-BK analog antibodies. The purified antibody is coupled to AFFI-GEL 10 (Bio-Rad, Richmond, Calif.) to form an affinity column. Immobilized anti-BK analog antibody, with the derivatized BK analog bound thereto, is then removed from the column by 0.2 M glycine elution and suspended in a solution of a second single chain BK analog. An ultraviolet light source (e.g., Mineralight UVSL-25, Ultra Violet Products, Inc., San Gabriel, Calif.) is positioned 1 cm from the gently stirred suspension and irradiated in a long-wavelength range for about 10 minutes. The suspension is put back on the anti-BK analog antibody affinity column and washed with a buffer containing 0.15 M NaCl, 0.1% bovine serum albumin, 0.01% polysorbate 80 and 25 KIU/ml of aprotinin to remove reaction byproducts. The covalently cross-linked dimer is eluted with the same buffer system containing 0.2 M glycine or 5 M guanidine. The eluted dimer is dialyzed against buffer to remove the chaotropic agent.

Following reaction with the BK analog under ultraviolet irradiation, and chromatography of the reaction mixture as above, the covalently cross-linked dimer is eluted with either 0.2 M glycine or 5 M guanidine.

While the above-described procedure utilizes SASD, a cleavable cross-linker, non-cleavable cross-linking reagents may be utilized which contain, e.g., alpha-hexanoate, rather than beta-ethyl-1,3-dithiopropopionate moieties. MSB is one example of a non-cleavable cross-linking reagent.

The single-chain BK analogs may be prepared by conventional solid phase peptide synthesis techniques using automated synthesis. Alternatively, BK analogs may be prepared by recombinant DNA techniques. A gene which encodes a BK analog may be constructed and introduced into an appropriate host by use of an appropriate cloning vector. Thus, it should be understood that the present invention is not merely limited to the use of BK analogs as prepared by peptide synthetic methods, but also includes polypeptides prepared by recombinant techniques.

Moreover, by utilization of such recombinant techniques, one skilled in the art may prepare additional BK analogs using methods such as site-directed mutagenesis of the relevant DNA, wherein an amino acid sequence may be modified to contain single or multiple amino acid changes, additions, or deletions.

Such sequence modifications are included within the scope of the invention, provided that the resulting molecule substantially retains the ability to inhibit thrombin-induced cell activation.

Additional BK analogs may be identified by screening a combinatorial library which displays a plurality of peptide analogs. As an example, degenerate oligonucleotides may be used to direct the display of heterologous peptides on the surface of microorganisms (for example, bacteriophage, bacteria, yeast). One such method uses a display library expressing the DNA sequence $(NNK)_n$. This DNA encodes the amino acid sequence $(Xaa)_n$, which includes all peptides having n amino acids. The number of possible peptides (using the 20 natural amino acids) is $20°$. Libraries of such microorganisms are initially screened for the ability to bind the cloned thrombin receptor or the NAT12 peptide, as described in Example 2. Peptides having activity in a binding assay are screened using one of the in vitro functional assays described in Example 1. Activity in the in vitro functional assays is predictive of activity in vivo, as shown in Example 3. New BK analogs which show activity in the in vitro functional assays are tested for safety and efficacy in animals and in human clinical trials.

Combinatorial libraries can also be prepared on a solid phase matrix support, and screened for the ability to bind to the thrombin cleavage site on the thrombin receptor. It is particularly advantageous to screen combinatorial libraries for compounds which (1) inhibit thrombin-induced platelet aggregation, (2) bind to the thrombin cleavage site on the thrombin receptor, and (3) inhibit thrombin-induced calcium mobilization in fibroblasts. This combination screening method identifies compounds which are selective inhibitors of thrombin-induced platelet and other cell activation. Additional methods of preparing and screening combinatorial libraries are known to those of skill in the art.

Purified BK analogs may be administered in any circumstance where inhibition of thrombin-induced or ADP-induced platelet activation or platelet aggregation is sought. BK analogs are administered to subjects experiencing platelet thrombosis from any cause, and may also be used prophylactically in subjects undergoing surgery or catherization for insertion of artificial dacron grafts and stents to prevent reocclusion events due to platelet thrombi. BK analogs may be infused into individuals to prevent strokes and cerebral edema.

The BK analogs may be administered by any convenient means which will result in substantial delivery into the bloodstream, including intravenous, intranasal, and oral administration, as well as administration via a dermal patch or rectal suppositories. Intravenous administration is presently contemplated as the preferred administration route, although intranasal administration may also be utilized. Since BK analogs are soluble in water, they may be effectively administered in solution. The actual dosage administered may take into account the size and weight of the patient, whether the nature of the treatment is prophylactic or therapeutic in nature, the age, health and sex of the patient, the route of administration, and other factors. Those skilled in the art can derive appropriate dosages and schedules of administration to suit the specific circumstances and needs of the patient. An effective daily dosage of active ingredients, based upon in vivo clearance studies using BK analogs related to those of the present invention, is from about 0.1 to about 10 grams per day per 70 Kg of body weight. The effective daily dosage is preferably from about 1 to about 5 grams per day per 70 Kg of body weight. In a preferred embodiment, a dosage of about 3 grams per day per 70 kg of body weight is given in a single bolus infusion of 2.4 grams followed by a continuous infusion of 0.025 g/hour.

The amount of BK analog administered will also depend upon the degree of platelet activation or aggregation inhibition that is desired. While infusion of a BK analog to achieve 3 grams per day dosage may be advantageously utilized, more or less of the peptide may be administered as needed. The therapeutic end point may be determined by monitoring platelet finction by aggregation and secretion, vessel patency, and bleeding. The actual amount of the BK analog administered and the length of the therapy regime to achieve the desired intravascular concentration is readily determinable by those skilled in the art by routine methods.

The BK analogs may be administered in a pharmaceutical composition in a mixture with a pharmaceutically acceptable carrier. The pharmaceutical composition may be compounded according to conventional pharmaceutical formulation techniques. The carrier may take a wide variety of forms depending on the form of preparation desired for administration. For a composition to be administered parenterally, the carrier will usually comprise sterile water, although other ingredients to aid solubility or for preservation purposes may be included. Injectable suspension may also be prepared, in which case appropriate liquid carriers, suspending agents and the like may be employed. The preferred parenteral route of administration is intravenous administration.

For intravenous administration, the BK analogs may be dissolved in any appropriate intravenous delivery vehicle containing physiologically compatible substances, such as sterile sodium chloride having a buffered pH compatible with physiologic conditions. Such intravenous delivery vehicles are known to those skilled in the art.

EXAMPLES

The following examples illustrate the practice of the invention. These examples are illustrative only, and do not limit the scope of the invention.

Example 1

In Vitro Functional Assays

Functional assays are used to evaluate the relative inhibitory efficacies of the methods and compounds according to the invention. In these assays, native BK (SEQ ID NO:5), the BK fragment Arg-Pro-Pro-Gly-Phe (SEQ ID NO:7), or another BK analog, may be used as a positive control peptide.

A. Inhibition of Platelet Aggregation

For human platelet aggregation studies, 50 ml human blood was collected into a syringe containing 5 ml of 0.013 M sodium citrate. The anticoagulated blood was centrifuged at 180 xg for 10 minutes at room temperature and the platelet-rich plasma was the supernatant. Platelet aggregation studies in platelet-rich plasma were performed in the cuvette of an aggregometer using γ-thrombin (Haematologic Technologies, Essex Junction, Vt.). After standardization of the aggregometer, the threshold dose of γ-thrombin, defined as the minimal concentration that will induce full platelet aggregation, was ascertained for each preparation of platelet-rich plasma. Typically, the threshold dose of γ-thrombin was between 5 and 30 nM.

Various concentrations of the peptide being tested were added to the platelet-rich plasma in the cuvette of the aggregometer. Platelet aggregation was induced by the addition of γ-thrombin. The degree of platelet aggregation was determined by measuring (in arbitrary units) the increase in light transmission through the stirred suspension of platelet-rich plasma.

In a control experiment, the BK fragment SEQ ID NO:7 inhibited γ-thrombin-induced (20 nM) platelet aggregation at a concentration of 1 mM peptide.

B. Inhibition of Platelet Aggregation and Secretion

For simultaneous platelet aggregation and secretion studies, fresh whole blood was collected and mixed with sodium citrate (final concentration 0.013 M). Platelet-rich plasma was prepared according to the method of Meloni et al., *J. Biol. Chem.* 266, 6786, 1991. Washed platelets were prepared by gel filtration over Sepharose 2B columns in Hepes-Tyrode's buffer (0.137 M NaCl, 3 mM KCl, 0.4 mM Na $H_2PO_4$, 12 mM $NaHCO_3$, 1 mM $MgCl_2$, 14.7 mM Hepes containing 20 mM glucose and 0.2% bovine serum albumin, pH 7.35). Platelets were incubated according to the method of Schmaier et al., *Blood* 56, 1013, 1980 with 5-[$^{14}$C] hydroxytryptamine for 30 min at 37° C. The washed platelets ($2 \times 10^8$/ml, final concentration radiolabeled with 5-[$^{14}$C] hydroxytryptamine) were added to a cuvette of an aggregometer (Chronolog Corp., Havertown, Pa.), standardized using the protocol of Meloni et al., supra. After the addition of $ZnCl_2$, final concentration 50 μM, purified HK (1 μM) or various concentrations of the peptides (0.1 to 3 mM) or buffer alone was added to the cuvette. Once the baseline stabilized, α-thrombin [0.125 U/ml (1 nM) final concentration] was then added to initiate platelet activation. Stirred platelets were allowed to incubate with α-thrombin and additions for 1 min. In other experiments, platelets were stimulated with TRAP (0.625 to 2.5 μM), ADP (1–5 μM) (Sigma), collagen (1.25 μg/ml) (Horm, Munich, Germany), or U-46619 (1 μM)(Calbiochem Behring, San Diego, Calif.). Additional experiments were performed with washed platelets stimulated with γ-thrombin (1 nM) in the presence of human fibrinogen (100 mg/dl). Both γ-thrombin and human fibrinogen were purchased from Enzyme Research Laboratories, South Bend, Ind. At the conclusion of the incubation, the entire platelet sample was centrifuged at 10,900×g (Model E, Beckman Instruments, Palo Alto, Calif.) over a 0.135 mM formaldehyde, 5 mM EDTA solution (1 part of fornaldehyde-EDTA to 4 parts of platelet suspension) and stored on ice until an aliquot of the supernatant was assayed for 5-[$^{14}$C]hydroxytryptamine secretion. Percent secretion was determined by the ratio of the loss of 5-[$^{14}$C]hydroxytryptamine in the supernatant of the agonist-treated specimen to the total 5-[$^{14}$C]hydroxytryptamine in a platelet suspension of unstimulated platelets after the level of 5-[$^{14}$C]hydroxytryptamine in the supernatant of the unstimulated sample was subtracted from both. Platelet aggregation was measured in arbitrary units as the initial rate of change in light transmittance in the first minute after introduction of agonist.

In a control experiment, native BK (SEQ ID NO:5) inhibited α-thrombin-induced (1 nM) platelet activation with an $IC_{50}$ of 0.25 mM and 1.0 mM for 100 percent aggregation and secretion inhibition, respectively.

C. Inhibition of α-thrombin-induced Calcium Mobilization

For calcium mobilization studies, the cytoplasmic free $Ca^{2+}$ concentration ([$Ca^{2+}$]$_i$) was measured using the fluorescent $Ca^{2+}$ indicator fura-2 acetyloxymethylester (fura-2 AM, Molecular Probes, Inc., Eugene, Oreg.). Gel filtered platelets in HEPES-Tyrode's buffer were loaded with fura-2 by incubation at 37° C. with 1 μM fura-2 AM for 45 min according to the method of Rasmussen et al., *J. Biol. Chem.* 268, 14322 (1993). The labeled platelets were then re-gel filtered to remove any excess probe. Aliquots of the labeled platelet suspension were transferred into a quartz cuvette with a magnetic stirrer, which was then placed in a thermostatically controlled chamber at 37° C. in a fluorescence spectrophotometer (Dual Wave Length Shimadzu SP5000 Spectrofluorometer, Shimadzu USA, Pittsburgh, Pa.). Reagents were directly added to the cuvette. The excitation wave lengths varied between 340 and 380 nm. The fluorescence was measured by recording emitted light at 510 nm as reported by Fisher et al., *Mol. Pharm.* 35, 195 (1989). The minimum emission was determined on a 20 mM digitonin, 10 mM EGTA solubilized platelet sample; maximum emission was determined on the same sample with 10 mM $Ca^{2+}$ added. The intraplatelet free $Ca^{2+}$ concentration was calculated by the method of Grykiewicz et al., *J. Biol. Chem.* 260, 3440 (1985). The ratio of the fluorescence readings was calculated as R=340/380 nm and processed according to the equation $[Ca^{2+}]_i = K_D((R-R_{min})/R_{max}-R))(S_{f2}/S_{b2})$ to determine the intraplatelet free $Ca^{2+}$ concentration. The $K_D$ for fura-2 was assumed to be 224 nM. $R_{max}$ and $R_{min}$ are the maximum and minimum fluorescence ratios measured at the end of the experiment, respectively; $S_{f2}$ and $S_{b2}$ are the fluorescence values at 380 nm in the absence and presence of saturating [$Ca^{2+}$], respectively.

In a control experiment, the BK fragment SEQ ID NO:7 was able to inhibit α-thrombin-induced calcium mobilization in a concentration dependent manner. One mM SEQ ID NO:7 produced 80% inhibition of α-thrombin-induced calcium mobilization. These data indicate that BK analogs can interfere with α-thrombin activation of platelets at the level of the stimulus-response coupling mechanism.

A variation of the calcium mobilization assay uses fibroblasts (which express a single receptor for thrombin, PAR 1), umbilical vein endothelial cells, or other cells which express the cloned thrombin receptor, and which grow in monolayers on the bottom of plastic wells. Examples of other kinds of cells which express the thrombin receptor, and which may have their calcium mobilization abilities blocked, include smooth muscle cells, astrocytes and neuronal cells.

Fibroblasts or endothelial cells were grown in 24–96 well plates and loaded with the fluorescent $Ca^{2+}$ indicator fura-2 acetyloxymethylester (5 μM, Molecular Probes Inc.) by incubation for 60 min. in HEPES-Tyrode's buffer at 37° C. After washing the cells, the fluorescence of the cells was monitored on a thermostatically controlled heated pad at 37° C. for 1 min, then the cells were incubated with α-thrombin (1 to 5 nM) in the absence or presence of a BK analog. Fluorescence was detected by a Perkin-Elmer LS-50B Luminescence Spectrofluorometer. Excitation was measured at 340 and 380 nm wavelength and emission was assessed at 510 nm. The cytosolic $Ca^{2+}$ levels were determined as described above. The $R_{max}$ value was determined using 10 mM $Ca^{2+}$ in the presence of 20 μM Ionophor A23187; $R_{min}$ was determined in the presence of 20 mM EDTA.

D. Inhibition of the Elimination of the Epitope Recognized by SPAN12

Flow cytometry studies were performed to determine whether BK analogs prevent α-thrombin from eliminating an epitope on the thrombin receptor which is lost following α-thrombin cleavage of the receptor. SPAN12 is an antibody to the thrombin receptor on platelets, which is specific for such an epitope.

Platelets for flow cytometry studies were prepared from 53.3 ml fresh blood anticoagulated with 8.7 ml acid citrate dextrose (10 mM trisodium citrate, 66 mM citric acid, 111 mM glucose, pH 4.6). Washed platelets from platelet-rich plasma were prepared by centrifugation at 180×g for 15 min. at room temperature. The platelet-rich plasma was brought to a final concentration of 2.8 μM with $PGE_1$ (Sigma) and 1:25 (vol:vol) with 1 M sodium citrate. After a 5 min. incubation at room temperature, the platelet-rich plasma was centrifuged at 1200×g for 10 min. at room temperature. The platelet pellet was then re-suspended in 10 ml of platelet wash buffer (128 mM NaCl, 4.26 mM $NaH_2PO_4$, 7.46 mM Na$_2$HPO$_4$, 4.77 mM sodium citrate, 2.35 mM citric acid, 5.5 mM glucose, 3.5 mg/ml bovine serum albumin, pH 6.5) followed by centrifugation at 1200×g for 5 min. at room temperature. After re-suspension in 5 ml of platelet suspension buffer (137 mM NaCl, 2.6 mM KCl, 13.8 mM NaHCO$_3$, 5.5 mM glucose, 1 mM MgCl$_2$, 0.36 mM NaH$_2$PO$_4$, 10 mM Hepes, 3.5 mg/ml bovine serum albumin, pH 7.35), the platelet count was adjusted to 400,000/µl. One hundred µl of washed platelets were then placed in a 5 ml round bottom polystyrene tube in the absence or presence of the BK analogs before treatment with α-thrombin (0.125 U/ml or 1 nM). Primary antibodies were added at a final concentration of 2 µg/ml and the antibodies were incubated with the platelets for 30 min at 4° C. After incubation, the platelets were diluted with 500 µl of platelet suspension buffer and again centrifuged at 1200×g for 5 min. at room temperature. The platelet pellets were then re-suspended in 100 µl of platelet suspension buffer and incubated with a 1:40 dilution of an anti-mouse IgG conjugated with FITC. After an additional incubation for 30 min. at 4° C., the platelets were again centrifuged at 1200×g for 5 min. followed by re-suspension in 500 µl of platelet suspension buffer.

Mouse IgG and an antibody to the epitope CD62 were used as controls. Mouse IgG (Code #4350) was purchased from BioSource, Camarillo, Calif. The fluorescence of bound FITC-anti-IgG to platelets was monitored on an Epics-C flow cytometer (Coulter Electronics, Hialeah, Fla.). Light scatter and fluorescence channels were set at logarithmic gain. Laser excitation was at 488 nm. Green fluorescence was observed through a 525 nm band pass filter. The relative fluorescence intensity of at least 15,000 platelets was analyzed in each sample. An antibody to CD62 (P-selectin) was purchased from Becton-Dickinson (Catalogue # 550014), San Jose, Calif.

SPAN12 detected an antigen on the thrombin receptor on unstimulated platelets. When the washed platelets were treated with 1 nM α-thrombin, there was a decrease in the antigenic expression of the epitope of the monoclonal antibody SPAN12. The forward scatter of the SPAN12 epitope seen on unstimulated platelets was shifted towards the origin on α-thrombin activated platelets, giving an absent antigen detection pattern similar to that for mouse IgG used as a control.

In a control experiment, 1 mM native BK (SEQ ID NO:5) prevented the loss of the epitope of the thrombin receptor on α-thrombin activated platelets.

E. Inhibition of α-thrombin Cleavage of NAT12

The peptide NAT12 (SEQ ID NO:2), which spans amino acids 35–46 of the α-thrombin cleavage site on the thrombin receptor (Vu et al., *Cell* 64, 1057 (1991), was also used to determine whether BK analogs blocked α-thrombin cleavage of the cloned receptor.

The cleavage studies were performed according to the method of Molino et al., *J. Biol. Chem.* 270, 11168 (1995). Briefly, NAT12 (SEQ ID NO:2) was dissolved in a solution of 0.01 M NaH$_2$PO$_4$ and 0.15 M NaCl, pH 7.4. The mixture was then incubated with 8 nM α-thrombin for one hour at 37° C. either in the absence (control) or presence of 1 mM of a BK analog. Following incubation, the mixture was applied to a Vyadec C-18 HPLC column in 0.1% trifluoroacetic acid and eluted with a gradient from 0% to 100% of 80% MeCN and 0.1% trifluoroacetic acid. The sizes of the separated products were confirmed by mass spectrometry.

NAT12 (SEQ ID NO:2) produced a single peak (peak 1) when analyzed by HPLC. When NAT12 was treated with α-thrombin, its peak area was reduced by 81% and two new peaks appeared, the new peaks constituting 44% (peak 3) and 37% (peak 2), respectively, of the original peak area. The additional peaks, peaks 3 and 2, represent the cleavage products of NAT12.

In a control experiment, in the presence of the BK fragment SEQ ID NO:7, peak 1 of NAT12 was reduced by only 57% after treatment with α-thrombin, and the cleavage products (peaks 3 and 2) of NAT12 constituted only 31% and 26%, respectively, of the original peak area.

Example 2

Binding Assays

Binding assays are used to show protein-protein interactions, and can be used to determine which domains of proteins participate in the binding and to ascertain the relative binding affinity of various domains. Binding assays are also used to screen large numbers of peptides, such as those in a combinatorial library. It is particularly useful to screen peptides for the ability to bind to the NAT12 peptide or to the thrombin receptor. Peptides that show activity in one or more of the binding assays are also tested in one or more of the in vitro functional assays, such as those described in Example 1. A combination of binding and functional assays can be used to identify compounds that selectively inhibit thrombin-induced platelet and other cell activation.

A. Assay for Binding to the NAT12 Peptide

Peptides from a combinatorial library are linked to microtiter plates and the wells are blocked with 1% BSA. Biotinylated-NAT12 is incubated with the microtiter plates. After washing, the presence of biotin-NAT12 attached to the matrix support expressing peptides is detected by incubation with ImmunoPure streptavidin horseradish peroxidase conjugate (Pierce Chemical Co., Rockville Ill.) followed by peroxidase-specific fast reacting substrate, turbo-3,3',5,5'-tetramethylbenzidine (turbo-TMB, Pierce Chemical Co., Rockville Ill.). After incubation for 5 min at room temperature, the color reaction of the turbo-TMB is stopped by the addition of 1 M phosphoric acid. The bound peptide is quantified by measuring the absorbance of the reaction mixture at 450 nm using a Microplate auto reader EL311 (BioTek Instrument, Winooski Vt.).

B. Assay for Binding to the Thrombin Receptor

Peptides from a combinatorial library on a solid phase matrix support are incubated with biotinylated thrombin receptor. The thrombin receptor may be expressed in bacterial, baculovirus, or other recombinant system, using methods known to those skilled in the art. Isolated receptor is biotinylated by procedures known to those skilled in the art. The labeled receptor is incubated with the peptides on the matrix support and detected as described for the NAT12 binding assay, above.

Example 3

In Vivo Clearance and Function: Correlation With In Vitro Results

Clearance studies were performed in New Zealand white rabbits weighing between 2.0 and 2.5 kg. Rabbits were premedicated according to the method of Michelson et al., *J. Mol. Cell Cardiol.* 20, 547 (1988) with 10 mg/kg 1 M xylazine and 10 mg/kg 1 M ketamine. After tracheostomy, intubation, and positive pressure ventilation done with room air (Harvard instruments), stage III surgical anesthesia was maintained with 20 mg/ml of intravenous pentobarbital. A carotid artery and a jugular vein were then exposed. A catheter was inserted into the exposed carotid artery for withdrawal of blood samples and monitoring the animal's blood pressure (Gould, Inc., Cardiovascular Products, Oxnard. Calif.). In a similar manner, a catheter was inserted into the exposed jugular vein for administering the anesthetic and BK analog.

A single intravenous infusion of BK analog was injected. The amount of BK analog injected was calculated from the weight of the animal such that the blood concentration was 1 mM peptide. For example: for a 2.5 kg rabbit, 7% of its weight gives an estimated blood volume of 175 ml. Accordingly, 89 mg of the control BK fragment SEQ ID NO:7 was injected (giving a 1 mM concentration in the 175 ml plasma). Depending upon the size of the animal, 75 to 90 mg peptide was injected. Blood samples were collected at 2, 4, 6, 8, 10, 20, 30, 40, 60, 90, and 120 minute intervals after infusion into a 0.013 M sodium citrate anticoagulant solution. Plasma was prepared from each of the blood samples collected over time by centrifugation of the blood samples at 10,000×g for two minutes. Aliquots of the plasmas were assayed for the presence of the BK analog antigen by the ELISA technique using a MARKIT-M [1–5] BK assay from Dainippon Pharmaceutical Co., Ltd., Osaka, Japan.

For the function inhibition study, New Zealand white rabbits weighing between 2.0 and 2.5 kg were surgically prepared as described above. After a single bolus infusion of BK analog calculated as described above. 5 ml blood samples were collected at 2. 6, 10, 30, 60, 90, 120, 150, 180, 210, and 240 minute intervals following infusion into a 0.013 M sodium citrate anticoagulant solution. The collected blood samples were centrifuged at 180×g (1000 rpms) for 15 minutes at room temperature. The platelet-rich plasma (PRP) portion of the blood was contained in the supernatant. The platelet count of the PRP, obtained with an H-10 Cell counter (Texas International Laboratories, Inc., Houston, Tex.), was adjusted with rabbit platelet-poor plasma to 200,000–250,000 platelets/$\mu$l.

Platelet aggregation studies on the PRP were conducted on a 4-channel aggregometer (BioData-PAP-4, Bio Data Corp., Hatboro, Pa.). The degree of platelet aggregation was determined by measuring the increase in light transmission through a stirred suspension of PRP maintained at 37° C. Platelet aggregation was induced in the PRP sample by addition of 20 $\mu$M ADP and $\gamma$-thrombin according to the method of Harfenist et al., *Thromb. Haemost.* 53, 183 (1985).

Like human platelets, rabbit platelets displayed a variable response to $\gamma$-thrombin. Each rabbit's platelets were evaluated before BK analog infusion for their threshold response to $\gamma$-thrombin. The rabbit platelets were typically responsive to 10 nM to 40 nM $\gamma$-thrombin. Simultaneous $\gamma$-thrombin-induced platelet aggregation studies were performed with 10, 20, and 40 nM $\gamma$-thrombin and 20 $\mu$M ADP.

Control experiments were performed using the BK fragment SEQ ID NO:7. The peak plasma concentration of BK fragment SEQ ID NO:7 after infusion was 60 $\mu$g/ml (0.120 mM) for two of three rabbits, as determined by ELISA. No unfavorable effects were observed in the animals following the bolus injection of the BK fragment. The rabbits' blood pressure, pulse, and platelet count remained stable and there was no abnormal bleeding at the surgical sites of cutdowns and intubations. The half-life of BK fragment SEQ ID NO:7 antigen clearance in plasma has two phases: one at 2.8 minutes and a second at 20 minutes after infusion.

The BK fragment SEQ ID NO:7 had a prolonged biologic clearance, however. After a single bolus infusion, 10 nM $\gamma$-thrombin-induced platelet aggregation was inhibited 100% for over 4 hours. 20 nM $\gamma$-thrombin-induced platelet aggregation was inhibited $\geq$50% for 2.75 hours, and 40 nM $\gamma$-thrombin-induced platelet aggregation was inhibited $\geq$50% for one hour. There was $\geq$50% inhibition of ADP-induced platelet aggregation for roughly 45 minutes.

These data demonstrate that after a single bolus infusion of BK analog, having a peak peptide concentration of only 0.120 mM two minutes after infusion, there was a prolonged, selective inhibitory effect on thrombin-induced and ADP-induced platelet activation in vivo.

When the peptide RPPGF (SEQ ID NO:7) was infused in vivo in rabbits, there was a prolonged inhibition of $\gamma$-thrombin-induced platelet aggregation in rabbit platelet-rich plasma ex vivo, as shown in FIG. 1.

A human platelet study was similar to the functional study using white rabbits described above. Briefly, blood samples were obtained from normal human volunteers. Platelet counts were measured with a Coulter counter, Model 2F (Coulter Hialeah, Fla.) and adjusted to a platelet count of 200,000 platelets/$\mu$l. Each individual's platelets at baseline were measured for their threshold response to $\gamma$-thrombin. Typical threshold levels were between 10 nM to 40 nM.

Human platelets in PRP were treated with 20 nM $\gamma$-thrombin. When 1 mM BK fragment SEQ ID NO:7 was reacted with 20 nM $\gamma$-thrombin, the aggregation tracing was abolished. The specificity of this reaction was demonstrated by comparing the results to those for a non-BK analog peptide (SEQ ID NO:8). SEQ ID NO:8 (1 mM) was unable to inhibit the ability of $\gamma$-thrombin to induce platelet activation.

Human platelets were treated with RPPGF (SEQ ID NO:7) in vitro. RPPGF (SEQ ID NO:7) appears to have a prolonged inhibitory effect. Human platelets in platelet-rich plasma were made 1 mM RPPGF (SEQ ID NO:7). After incubation for 1 h at 37° C., the platelet-rich plasma was centrifuged into a pellet, the plasma removed, and the pellet was resuspended in platelet-poor plasma without RPPGF (SEQ ID NO:7). After resuspension of the RPPGF-treated platelets in platelet-rich plasma, their ability to respond to $\gamma$-thrombin was compared with untreated platelet-rich plasma. In all instances examined, the concentration of $\gamma$-thrombin that served as the threshold to induce full platelet aggregation of RPPGF-treated platelet-rich plasma was greater than that seen with simultaneous control platelet-rich plasma. Further at the concentration of $\gamma$-thrombin that induced full aggregation of control platelet-rich plasma, each of the RPPGF-treated platelets was inhibited 62% or more. These data indicate that RPPGF (SEQ ID NO:7) bound to platelets actually increased their threshold for platelet aggregation induced by $\gamma$-thrombin.

Example 4

Preparation of BK Analogs

A. Preparation of Peptides

Peptides analogs of BK were synthesized on an Applied Biosystems Model 431 peptide synthesizer. The carboxy-terminal amino acid was covalently attached to a solid phase support, and succeeding amino acids were coupled sequentially to the amino terminus unless otherwise stated. The carboxyl group on the amino acid to be attached was activated with 2-(1-H-benzotriazole-1-YL)-1,1,3,3-tetramethyluroniumhexofluorophosphate (HBTU) and 1-hydroxybenzotriazole (HOBt). The fluorenyl-methyloxycarbonyl moiety was then attached at the amino-terminal end as a blocking group. Peptides were purified by preparative reverse-phase HPLC.

Synthesis of the peptide Arg-Pro-Pro-Amide was initiated on 4-(2',4'dimethoxyphenyl)-fmoc-aminomethylphenoxy resin. Once the fmoc group was removed, synthesis proceeded with attachment of the proline.

The peptides (D-Arg)-Pro-Pro and Arg-(D-Pro)-Pro were synthesized using standard methods known in the art.

B. Preparation of RPP MAP-4

"MAP" is an acronym for "multiple antigenic peptide". A four-branch MAP of RPP, hereinafter called "RPP MAP-4", was prepared. The structure of RPP MAP4 was as follows:

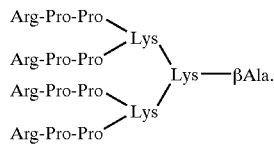

To prepare RPP MAP-4, a resin core, having a β-alanine attached through its carboxyl group, was joined to a free carboxyl of lysine through the free amine of β-alanine (βAla) to form a lysine-β-alanine complex. Two additional lysine residues were then attached by their free carboxyl groups to the two free amines of the first lysine. Four molecules of RPP were then attached through their proline residues to the free amino groups of the two lysine residues, following activation with HBTU and HOBt as described above. The RPP MAP-4 was purified by reverse phase HPLC and then characterized by mass spectroscopy.

Using similar methods, a "PP MAP-4 peptide" (a four-branch MAP of Pro-Pro) and a "RPPGF MAP-4 peptide" (a four-branch MAP of Arg-Pro-Pro-Gly-Phe) were also synthesized.

C. Preparation of RPP Heterodimer

A heterodimer of RPP was prepared. Lysine was attached to the amide resin, 4-(2',4'dimethoxyphenyl)-fmoc-aminomethylphenoxy resin. After its fmoc group was removed, RPP was synthesized as described above with the lysine attached to its carboxy terminus to yield RPPK. Treatment of the C-terminal lysine with hydrazine and dimethylformamide results in a free amino group to which an aspartic acid was attached. RPP was then synthesized from the C-terminal aspartic acid by standard techniques, resulting in the heterodimer shown below.

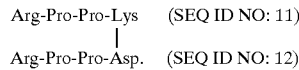

Arg-Pro-Pro-Lys    (SEQ ID NO: 11)
       |
Arg-Pro-Pro-Asp.   (SEQ ID NO: 12)

Example 5

BK Analogs Inhibit Thrombin-Induced Platelet Activation In Human Platelets In Vitro The peptides synthesized in Example 4 were assayed for the ability to inhibit γ-thrombin-induced platelet aggregation in platelet-rich plasma.

A. Inhibitory Activity of RPPGF and RPPAF

The BK analogs Arg-Pro-Pro-Ala-Phe ("RPPAF", SEQ ID NO: 6) and Arg-Pro-Pro-Gly-Phe ("RPPGF", a fragment of native BK, SEQ ID NO:7) both showed inhibition of γ-thrombin-induced platelet aggregation in an aggregation assay like the one described in Example 1A.

B. Inhibitory Activity of RPP, RPP MAP4, and RPP Heterodimer

The BK analogs Arg-Pro-Pro ("RPP"), RPP MAP4, and RPP heterodimer all showed inhibition of γ-thrombin-induced platelet aggregation in an aggregation assay like the one described in Example 1A.

Figure 2:
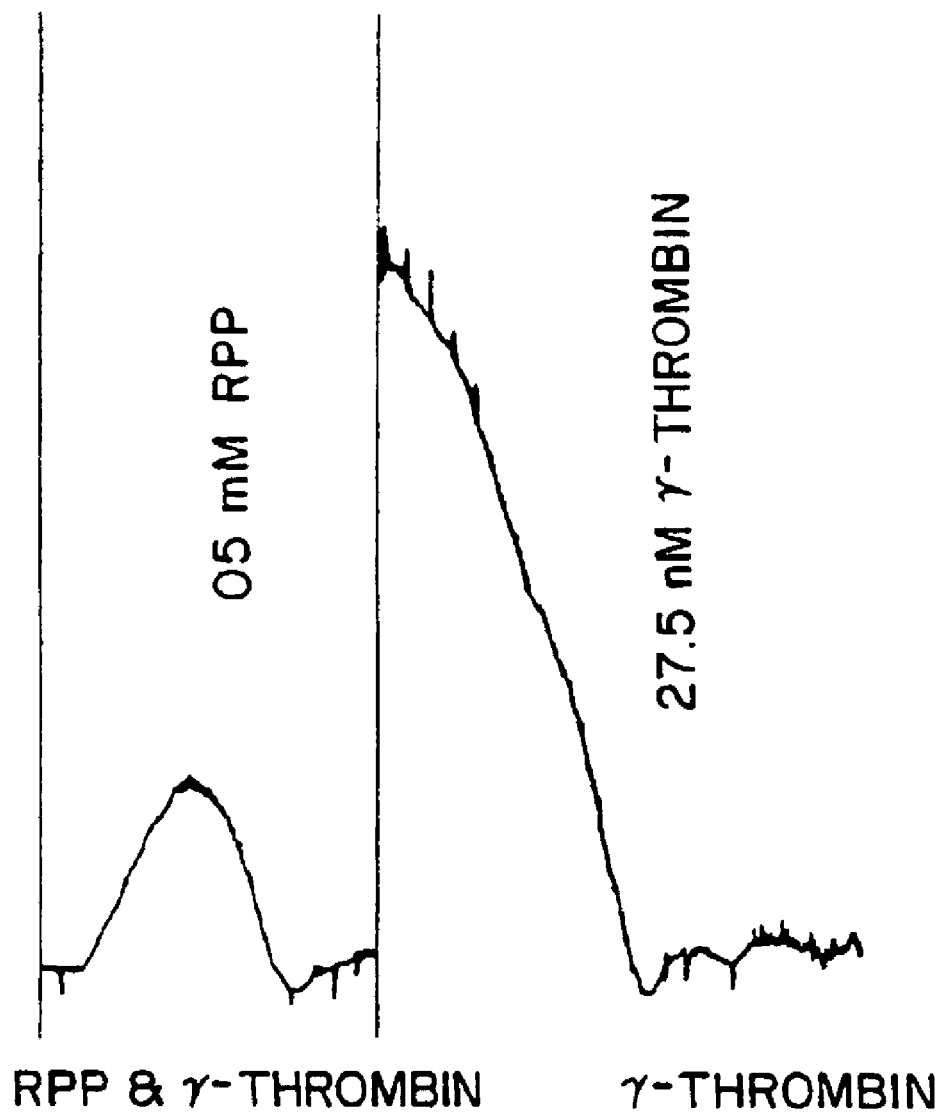
FIG. 2 shows aggregometer tracings of γ-thrombin induced aggregation of human platelets in platelet-rich plasma treated with γ-thrombin alone (control), and with the BK analog Arg-Pro-Pro (50 μM).

As shown in FIG. 2, RPP at 50 μM was able to abolish 27.5 nM γ-thrombin-induced platelet aggregation. In three experiments, RPP inhibited γ-thrombin-induced platelet aggregation 100% at a concentration of 0.089 mM±0.04 (mean±SD). RPP was greater than 2.5-fold better as an inhibitor than RPPGF, which under the same conditions inhibited γ-thrombin-induced platelet aggregation 100% at a concentration of 0.23 mM±0.12.

The peptides RPP-Amide, (D-Arg)-Pro-Pro, and Arg-(D-Pro)-Pro had reduced ability to inhibit γ-thrombin-induced platelet aggregation when compared to RPP itself. The dipeptide Arg-Pro had no inhibitory activity on γ-thrombin-induced platelet aggregation.

Figure 3:
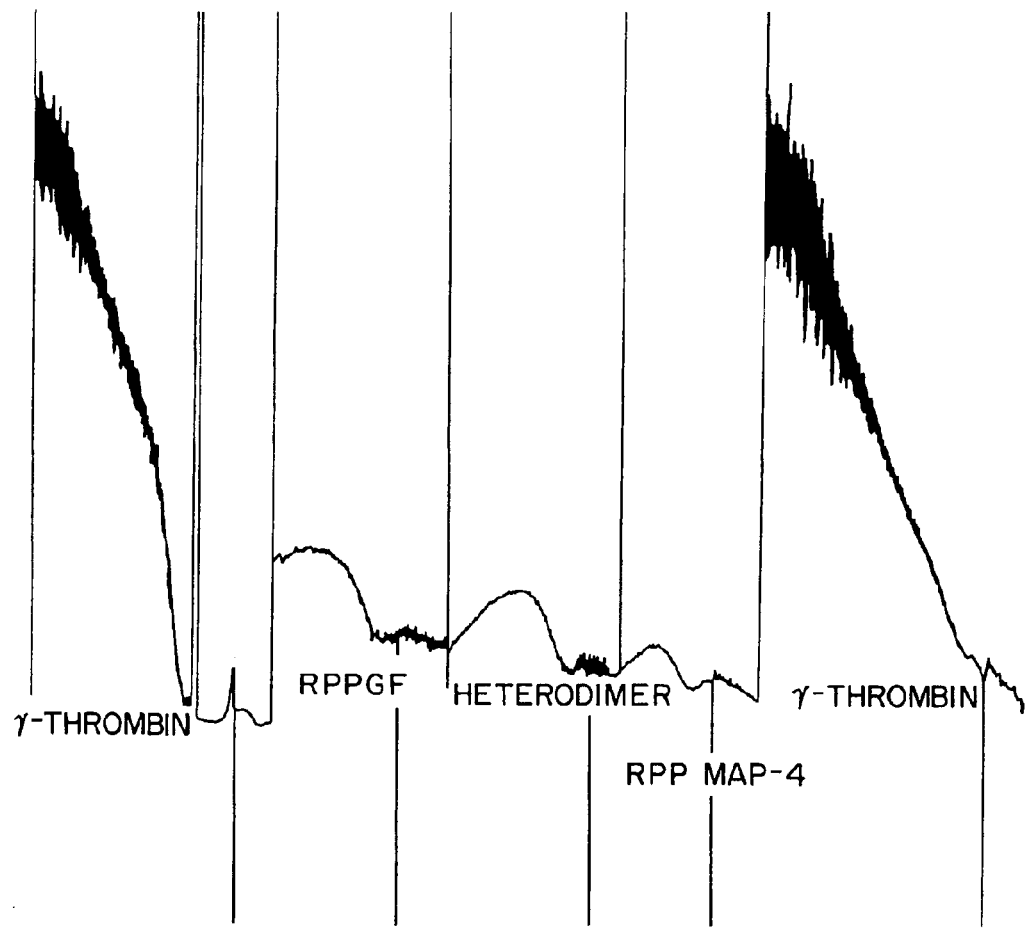
FIG. 3 shows aggregometer tracings of γ-thrombin induced aggregation of human platelets treated with γ-thrombin alone (control), with the peptide Arg-Pro-Pro-Gly-Phe (SEQ ID NO: 7, 125 μM), with a RPP heterodimer peptide (75 μM), and with a RPP MAP-4 peptide (25 μM).

As shown in FIG. 3, RPP MAP-4 inhibited γ-thrombin-induced platelet aggregation 100% at a concentration of 47 μM peptide (0.047 mM±0.019, mean±SD of 5 experiments). A PP MAP-4 peptide had no inhibitory activity on γ-thrombin-induced platelet activation.

As shown in FIG. 3, the heterodimer of RPP (HETERODIMER) inhibited γ-thrombin-induced platelet aggregation 100% at 75 μM peptide (0.079 mM±0.032, a mean±SD of 5 experiments). The inhibitory activity of the heterodimer was better than that of RPPGF but equal to that of RPP.

Example 6

BK Analogs Bind to the Thrombin Receptor Cleavage Site (NAT 12)

Figure 4:
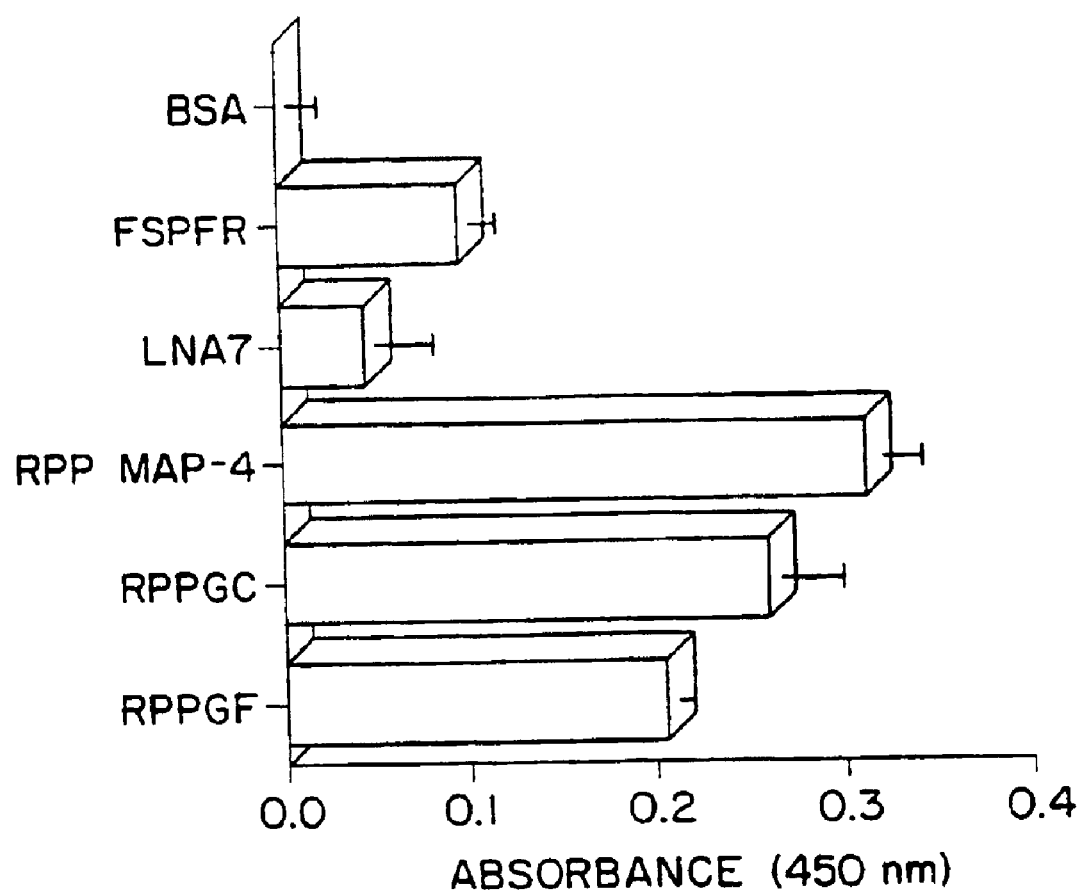
FIG. 4 shows the direct binding of biotinylated-NAT12 (SEQ ID NO:2) to RPPGF (SEQ ID NO:7), RPPGC (SEQ ID NO:9). RPP MAP-4, LNA7 (SEQ ID NO:8). FSPFR (SEQ ID NO:10), or bovine serum albumin (BSA).
Figure 5A:
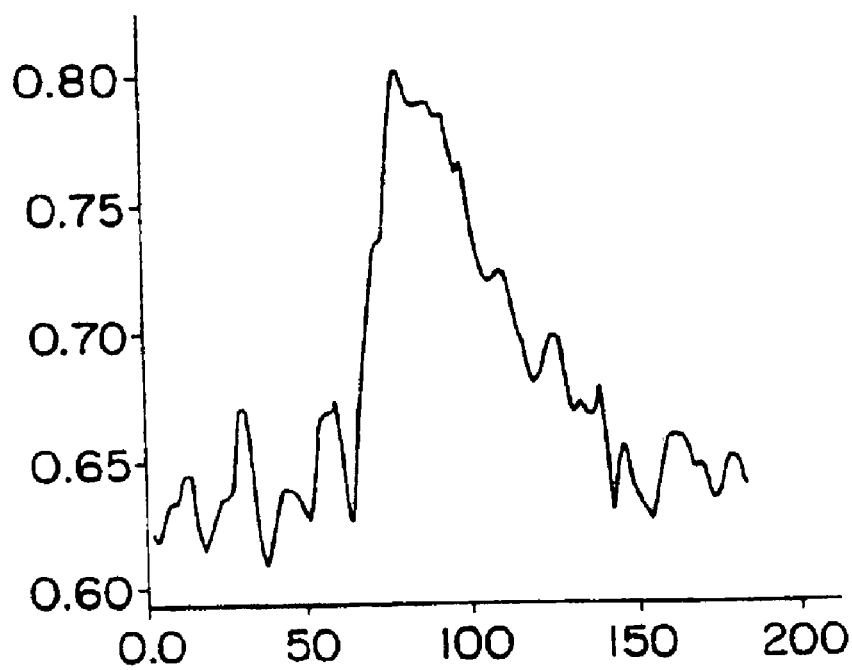
FIGS. 5A and 5B, 5C, and 5D show α-thrombin-induced calcium mobilization on fibroblasts grown to confluence in microtiter plates (panel A), and inhibition of α-thrombin-induced calcium mobilization by HK, high molecular weight kininogen (panel B), RPPGF (SEQ ID NO: 7, panel C), and RPP (panel D).
Figure 5B:
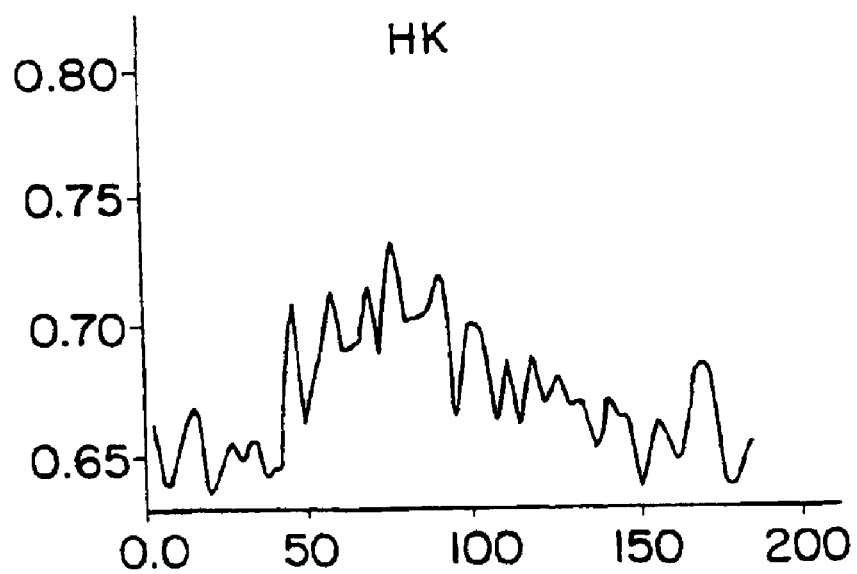
Figure 5C:
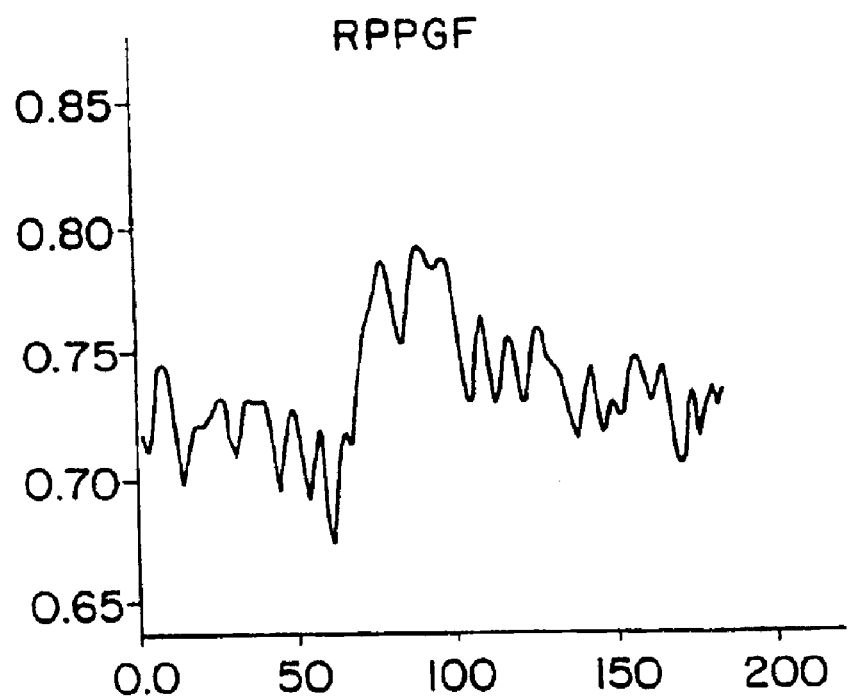
Figure 5D:
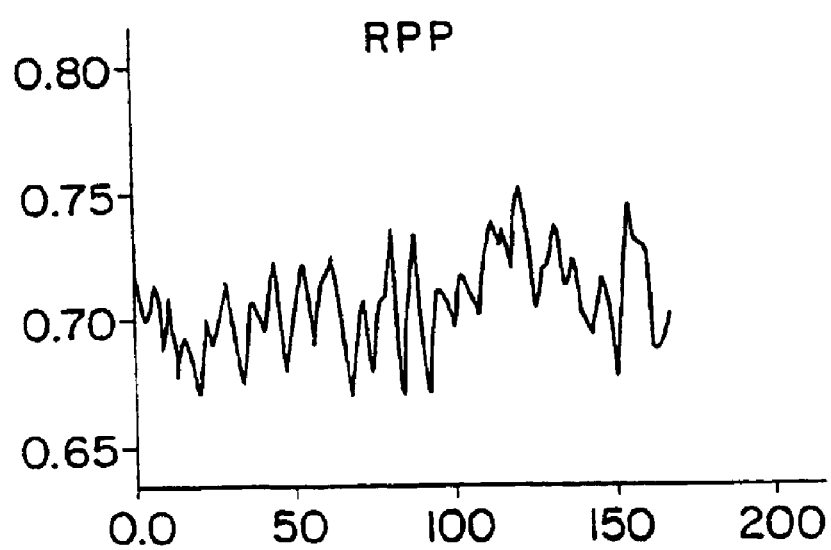
Figure 6A:
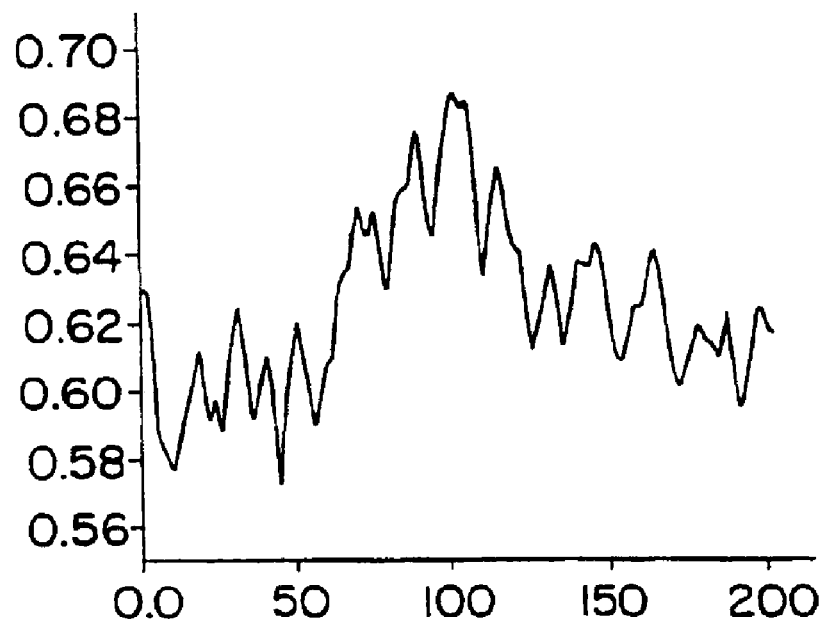
FIGS. 6A, 6B, 6C, and 6D show α-thrombin-induced calcium mobilization on human umbilical vein endothelial cells (HUVEC) grown to confluence in microtiter plates (panel A), and inhibition of α-thrombin-induced calcium mobilization by HK, high molecular weight kininogen (panel B), RPP MAP-4 (panel C), and RPPGF MAP-4 (panel D).
Figure 6B:
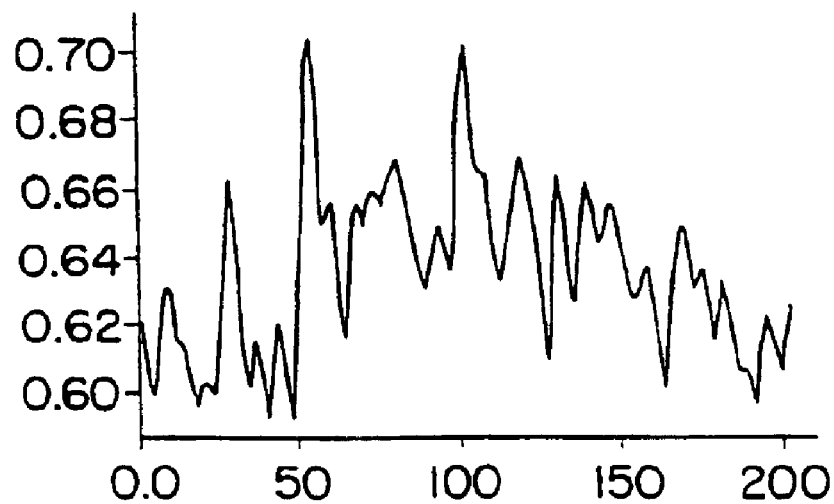
Figure 6C:
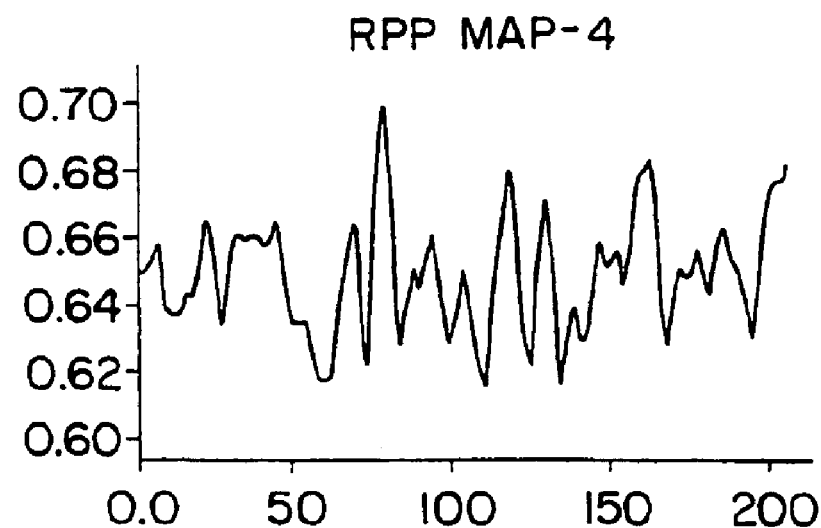
Figure 6D:
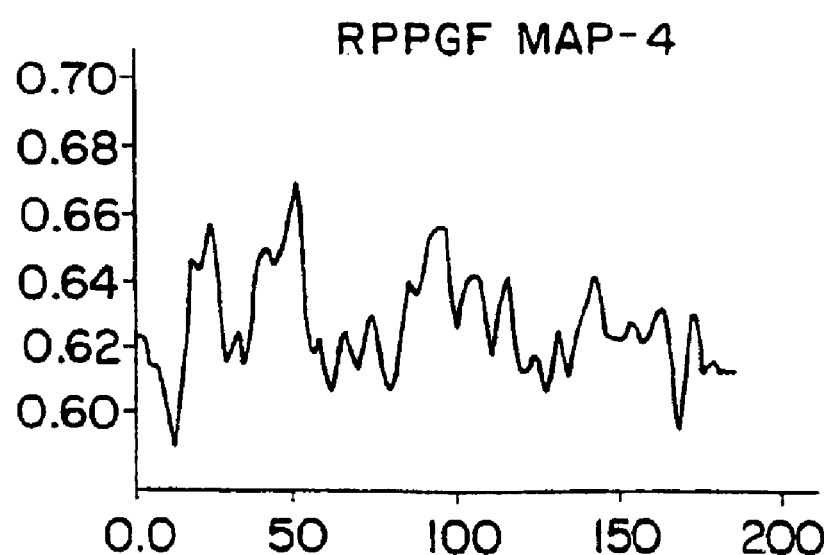

The specific binding of biotinylated NAT12 to BK analogs and other peptides was assayed as described in Example 2A. The results are shown in FIG. 4. Biotinylated NAT12 specifically bound to RPPGF (SEQ ID NO:7), RPPGC (SEQ ID NO:9), and RPP MAP4, but not peptides LNA7 (SEQ ID NO:8) or FSPFR (SEQ ID NO: 10).

Example 7

BK Analogs Inhibit α-thrombin-induced Calcium Mobilization in Fibroblasts and HUVEC Cells The ability of BK analogs to inhibit α-thrombin-induced calcium mobilization in fibroblasts and human umbilical vein endothelial cells (HUVEC) was assayed as described in Example 1C. As shown in FIGS. 5 and 6, HK, RPPGF (SEQ ID NO: 7), and RPP inhibited calcium mobilization in fibroblasts and HK, RPP MAP-4, and RPPGF MAP4 inhibited calcium mobilization in endothelial cells.

Example 8

Screening a Combinatorial Library to Identify BK Analogs

A. Screening for Ability to Bind the NAT12 Peptide

Peptides from a combinatorial library are linked to a microtiter plate and blocked with 1% BSA. Biotinylated-NAT12 is incubated with the microtiter plate. After washing, the presence of biotin-NAT12 attached to the matrix support expressing peptides is detected by incubation with Immu-noPure streptavidin horseradish peroxidase conjugate (Pierce Chemical Co., Rockville Ill.) followed by peroxidase-specific fast reacting substrate, turbo-3,3',5,5'-tetramethylbenzidine (turbo-TMB, Pierce Chemical Co., Rockville Ill.). After incubation for 5 min at room temperature, the color reaction of the turbo-TMB is stopped by the addition of 1 M phosphoric acid. The bound peptide is quantified by measuring the absorbance of the reaction mixture at 450 nm using a Microplate auto reader EL311 (BioTek Instrument, Winooski Vt.). Compounds which bind the NAT12 peptide are also assayed for the ability to inhibit platelet aggregation and the ability to inhibit calcium mobilization, using the assays described in Example 1.

B. Screening for Ability to Bind Thrombin Receptor

Recombinant thrombin receptor is biotinylated, then incubated with peptides from a combinational library on a solid phase matrix support. Binding of the labeled receptor is detected as described above.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A method of inhibiting thrombin-induced cell activation mediated by cleavage of a thrombin receptor on said cells comprising administering to an individual in need of such treatment an effective amount of a compound selected from the group consisting of:

(a) Arg-Pro-Pro;

(b) Arg-Pro-Pro-Ala-Phe (SEQ ID NO:6);

(c)

Arg-Pro-Pro-Lys
       |
   Arg-Pro-Pro-Asp;   and (d)

Arg-Pro-Pro\
               >Lys\
   Arg-Pro-Pro/     \
                     Lys—βAla.
   Arg-Pro-Pro\     /
               >Lys/
   Arg-Pro-Pro/

2. A method for preventing thrombin-induced platelet aggregation mediated by cleavage of a thrombin receptor on said platelets comprising administering to an individual in need of such treatment an effective amount of a compound selected from the group consisting of:

(a) Arg-Pro-Pro;

(b) Arg-Pro-Pro-Ala-Phe (SEQ ID NO:6);

(c)

Arg-Pro-Pro-Lys
       |
   Arg-Pro-Pro-Asp;   and (d)

Arg-Pro-Pro\
               >Lys\
   Arg-Pro-Pro/     \
                     Lys—βAla.
   Arg-Pro-Pro\     /
               >Lys/
   Arg-Pro-Pro/

3. A pharmaceutical composition comprising a pharmaceutically acceptable carrier and the compound Arg-Pro-Pro-Ala-Phe (SEQ ID NO:6).

4. A pharmaceutical composition comprising a pharmaceutically acceptable carrier and a compound having a formula selected from the group consisting of:

(a)

Arg-Pro-Pro-Lys
       |
   Arg-Pro-Pro-Asp;   and (b)

Arg-Pro-Pro\
               >Lys\
   Arg-Pro-Pro/     \
                     Lys—βAla.
   Arg-Pro-Pro\     /
               >Lys/
   Arg-Pro-Pro/

5. The method according to claim 1 wherein the compound is Arg-Pro-Pro.

6. The method according to claim 1 wherein the compound is Arg-Pro-Pro-Ala-Phe (SEQ ID NO:6).

7. The method according to claim 1 wherein the compound is

Arg-Pro-Pro-Lys
       |
   Arg-Pro-Pro-Asp.

8. The method according to claim 1 wherein the compound is
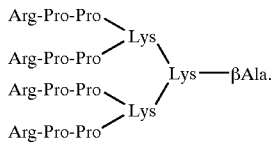
9. The method according to claim 2 wherein the compound is Arg-Pro-Pro.
10. The method according to claim 2 wherein the compound is Arg-Pro-Pro-Ala-Phe (SEQ ID NO:6).
11. The method according to claim 2 wherein the compound is:
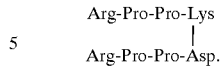
12. The method according to claim 2 wherein the compound is:
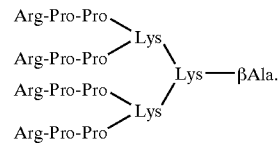
* * * * *